US008467497B2

(12) United States Patent
Lu et al.

(10) Patent No.: US 8,467,497 B2
(45) Date of Patent: Jun. 18, 2013

(54) SYSTEM AND METHOD FOR MOTION ADAPTIVE OPTIMIZATION FOR RADIATION THERAPY DELIVERY

(75) Inventors: Weiguo Lu, Madison, WI (US); Mingli Chen, Madison, WI (US); Quan Chen, Madison, WI (US); Kenneth J. Ruchala, Madison, WI (US); Gustavo H. Olivera, Madison, WI (US)

(73) Assignee: Tomotherapy Incorporated, Madison, WI (US)

( * ) Notice: Subject to any disclaimer, the term of this patent is extended or adjusted under 35 U.S.C. 154(b) by 45 days.

(21) Appl. No.: 12/398,869

(22) Filed: Mar. 5, 2009

(65) Prior Publication Data
US 2009/0252291 A1   Oct. 8, 2009

Related U.S. Application Data

(63) Continuation-in-part of application No. 12/259,038, filed on Oct. 27, 2008.

(60) Provisional application No. 60/982,605, filed on Oct. 25, 2007, provisional application No. 61/034,009, filed on Mar. 5, 2008.

(51) Int. Cl.
*A61N 5/10* (2006.01)
*A61N 5/01* (2006.01)
*A61B 5/05* (2006.01)

(52) U.S. Cl.
USPC .............. 378/65; 378/901; 600/427; 600/429

(58) Field of Classification Search
USPC .............. 378/64, 65, 68, 69, 210, 901; 600/1, 600/427–429; 607/100; 604/20; 128/605
See application file for complete search history.

(56) References Cited

U.S. PATENT DOCUMENTS

| 4,455,609 | A | * | 6/1984 | Inamura et al. .......... 250/370.07 |
| 5,027,818 | A | | 7/1991 | Bova et al. |
| 5,044,354 | A | | 9/1991 | Goldhorn et al. |
| 5,117,829 | A | | 6/1992 | Miller et al. |
| 5,138,647 | A | | 8/1992 | Nguyen et al. |
| 5,332,908 | A | | 7/1994 | Weidlich |
| 5,446,548 | A | | 8/1995 | Gerig et al. |

(Continued)

FOREIGN PATENT DOCUMENTS

| JP | 63209667 | 8/1988 |
| JP | 6007464 | 1/1994 |

(Continued)

OTHER PUBLICATIONS

Purdy, James, "3D Treatment Planning and Intensity-Modulated Radiation Therapy," Oncology, vol. 13, No. 10, suppl. 5 (Oct. 1999).

(Continued)

*Primary Examiner* — Anastasia Midkiff
(74) *Attorney, Agent, or Firm* — Michael Best & Friedrich LLP

(57) ABSTRACT

A system and method of optimizing delivery of a radiation therapy treatment. The system optimizes treatment delivery in real-time to take into account a variety of factors, such as patient anatomical and physiological changes (e.g., respiration and other movement, etc.), and machine configuration changes (e.g., beam output factors, couch error, leaf error, etc.).

30 Claims, 23 Drawing Sheets

U.S. PATENT DOCUMENTS

| | | | |
|---|---|---|---|
| 5,511,549 A | 4/1996 | Legg et al. | |
| 5,552,605 A | 9/1996 | Arata | |
| 5,579,358 A | 11/1996 | Lin | |
| 5,748,703 A | 5/1998 | Cosman | |
| 5,818,902 A * | 10/1998 | Yu | 378/65 |
| 5,823,192 A | 10/1998 | Kalend et al. | |
| 5,835,562 A | 11/1998 | Ramsdell et al. | |
| 5,870,697 A | 2/1999 | Chandler et al. | |
| 5,949,080 A | 9/1999 | Ueda et al. | |
| 6,049,587 A * | 4/2000 | Leksell et al. | 378/65 |
| 6,144,875 A | 11/2000 | Schweikard et al. | |
| 6,260,005 B1 | 7/2001 | Yang et al. | |
| 6,301,329 B1 | 10/2001 | Surridge | |
| 6,477,229 B1 | 11/2002 | Grosser | |
| 6,484,049 B1 | 11/2002 | Seeley et al. | |
| 6,530,873 B1 | 3/2003 | Lee | |
| 6,539,247 B2 | 3/2003 | Spetz | |
| 6,757,355 B1 | 6/2004 | Siochi | |
| 6,810,107 B2 | 10/2004 | Steinberg | |
| 6,853,702 B2 | 2/2005 | Renner | |
| 6,865,254 B2 | 3/2005 | Nafstadius | |
| 6,888,919 B2 | 5/2005 | Graf | |
| 6,914,959 B2 | 7/2005 | Bailey et al. | |
| 6,915,005 B1 | 7/2005 | Ruchala et al. | |
| 6,932,807 B1 | 8/2005 | Tomita et al. | |
| 6,961,405 B2 | 11/2005 | Scherch | |
| 6,977,984 B2 | 12/2005 | Hsieh et al. | |
| 7,043,058 B2 | 5/2006 | Cornog et al. | |
| 7,054,413 B2 | 5/2006 | Steinberg | |
| 7,116,749 B2 | 10/2006 | Besson | |
| 7,123,758 B2 | 10/2006 | Jeung et al. | |
| 7,142,635 B2 | 11/2006 | Kamath et al. | |
| 7,177,386 B2 | 2/2007 | Mostafavi et al. | |
| 7,221,729 B2 | 5/2007 | Wakai et al. | |
| 7,265,356 B2 | 9/2007 | Pelizzari et al. | |
| 7,283,610 B2 | 10/2007 | Low et al. | |
| 7,289,599 B2 | 10/2007 | Seppi et al. | |
| 7,302,033 B2 | 11/2007 | Carrano et al. | |
| 7,349,730 B2 | 3/2008 | Ein-Gal | |
| 7,382,858 B2 | 6/2008 | Gohno | |
| 7,444,011 B2 | 10/2008 | Pan et al. | |
| 7,450,687 B2 | 11/2008 | Yeo et al. | |
| 7,492,858 B2 | 2/2009 | Partain et al. | |
| 7,519,150 B2 | 4/2009 | Romesberg et al. | |
| 7,536,219 B2 | 5/2009 | Mitschke | |
| 7,551,717 B2 | 6/2009 | Tome et al. | |
| 7,590,440 B2 | 9/2009 | Lu et al. | |
| 7,611,452 B2 | 11/2009 | Allison et al. | |
| 7,613,501 B2 | 11/2009 | Scherch | |
| 7,616,729 B2 | 11/2009 | Vengrinovich et al. | |
| 7,645,276 B2 | 1/2010 | Pankratov et al. | |
| 7,831,289 B2 | 11/2010 | Riker et al. | |
| 7,945,021 B2 | 5/2011 | Shapiro et al. | |
| 7,945,022 B2 | 5/2011 | Nelms et al. | |
| 7,983,380 B2 | 7/2011 | Guertin et al. | |
| 8,085,899 B2 | 12/2011 | Nord et al. | |
| 8,125,813 B2 | 2/2012 | Nizin et al. | |
| 2003/0112922 A1 * | 6/2003 | Burdette et al. | 378/65 |
| 2003/0128807 A1 * | 7/2003 | Kotler et al. | 378/64 |
| 2003/0212325 A1 | 11/2003 | Cotrutz et al. | |
| 2004/0254448 A1 | 12/2004 | Amies et al. | |
| 2004/0260142 A1 * | 12/2004 | Lovoi | 600/1 |
| 2005/0171396 A1 | 8/2005 | Pankratov et al. | |
| 2005/0201516 A1 * | 9/2005 | Ruchala et al. | 378/65 |
| 2006/0072699 A1 * | 4/2006 | Mackie et al. | 378/4 |
| 2006/0078086 A1 | 4/2006 | Riley et al. | |
| 2006/0153330 A1 | 7/2006 | Wong et al. | |
| 2006/0241332 A1 * | 10/2006 | Klein et al. | 600/1 |
| 2007/0041495 A1 * | 2/2007 | Olivera et al. | 378/65 |
| 2007/0041496 A1 | 2/2007 | Olivera et al. | |
| 2007/0104316 A1 * | 5/2007 | Ruchala et al. | 378/65 |
| 2007/0197908 A1 | 8/2007 | Ruchala et al. | |
| 2008/0002809 A1 * | 1/2008 | Bodduluri | 378/41 |
| 2008/0002811 A1 * | 1/2008 | Allison | 378/65 |
| 2008/0008291 A1 | 1/2008 | Alakuijala et al. | |
| 2008/0031406 A1 | 2/2008 | Yan et al. | |
| 2008/0049896 A1 * | 2/2008 | Kuduvalli | 378/65 |
| 2008/0064953 A1 * | 3/2008 | Falco et al. | 600/427 |
| 2008/0159478 A1 * | 7/2008 | Keall et al. | 378/65 |
| 2008/0193006 A1 | 8/2008 | Udupa et al. | |
| 2008/0279328 A1 | 11/2008 | Zeitler et al. | |
| 2009/0041200 A1 | 2/2009 | Lu et al. | |
| 2009/0116616 A1 * | 5/2009 | Lu et al. | 378/65 |
| 2010/0053208 A1 | 3/2010 | Menningen et al. | |
| 2010/0054413 A1 | 3/2010 | Sobering et al. | |
| 2010/0119032 A1 * | 5/2010 | Yan et al. | 378/4 |
| 2011/0019889 A1 | 1/2011 | Gering et al. | |
| 2011/0112351 A1 | 5/2011 | Fordyce et al. | |

FOREIGN PATENT DOCUMENTS

| | | |
|---|---|---|
| JP | 10052421 | 2/1998 |
| JP | 10501151 | 2/1998 |
| JP | 11244401 | 9/1999 |
| JP | 2001161839 | 6/2001 |
| JP | 2001340474 | 12/2001 |
| JP | 2002210029 | 7/2002 |
| JP | 2002522128 | 7/2002 |
| JP | 2002522129 | 7/2002 |
| JP | 2003523220 | 8/2003 |
| JP | 2004166975 | 6/2004 |
| JP | 2004275636 | 10/2004 |
| JP | 2004321502 | 11/2004 |
| JP | 2005160804 | 6/2005 |
| JP | 2005518908 | 6/2005 |
| JP | 2007509644 | 4/2007 |
| TW | 300853 | 3/1997 |
| TW | I223199 | 11/2004 |
| TW | 261523 | 9/2006 |
| WO | 9014129 | 11/1990 |
| WO | 9202277 | 2/1992 |
| WO | 0007669 | 2/2000 |
| WO | 0054689 | 9/2000 |
| WO | 03092789 | 11/2003 |
| WO | 2004064641 | 8/2004 |
| WO | 2004066211 | 8/2004 |
| WO | 2004080522 | 9/2004 |
| WO | 2004105574 | 12/2004 |
| WO | 2005036124 | 4/2005 |
| WO | 2005057463 | 6/2005 |
| WO | 2005062790 | 7/2005 |
| WO | 2007079854 | 7/2007 |
| WO | 2007133932 | 11/2007 |

OTHER PUBLICATIONS

Birkner, M. et al., "Image guided adaptive IMRT of the prostate based on a probabilistic patient geometry," Radiotherapy and Oncology, vol. 64, Supplement 1, 21st Annual ESTRO Meeting, Sep. 21, 2002, p. S282, ISSN 0167-8140.

Yu, Cedric X., et al., "A Method for Implementing Dynamic Photon Beam Intensity Modulation using Independent Jaws and a Multileaf Collimator," Phys. Med. Biol. 40. 1995: 769-787.

Yan, Di, "On-line Strategy of Daily Dose Prescription in Adaptive Radiotherapy," Proceedings of the 22nd Annual EMBS International Conference, Jul. 23-28, 2000, Chicago, IL, pp. 2145-2148.

Lee, Jason et al., "Intensity Modulated Radiation Therapy; An Introduction for Patients and Clinicians," www.oncolink.com/templates/treatment/article.cfm?c=45&s=33&id=182; Jun. 16, 2001.

Keall, Paul, "4-Dimensional Computed Tomography Imaging and Treatment Planning," Seminars in Radiation Oncology, vol. 14, No. 1, Jan. 2004; pp. 81-90.

Lof, J. et al., "An Adaptive Control Algorithm for Optimization of Intensity Modulated Radiotherapy Considering Uncertainties in Beam Profiles, Patient Set-Up and Internal Organ Motion", Physics in Medicine and Biology 43, 1605-1628, Printed in the UK, 1998.

MacKie, T. Rockwell et al., "Tomotherapy" Seminars in Radiation Oncology, vol. 9, No. 1, Jan. 1, 1999, pp. 108-117, XP002603992.

Miller, Karen, "The Phantom Torso", RT Image, vol. 14 No. 25, Jun. 18, 2001.

Selker, Robert G., "Intensity Modulated Radiation Therapy (IMRT) Technology, The Peacock System, At the Western Pennsylvania Hospital," Archived Oct. 9, 1999, http://web.archive.org/web/19991009052520/http://virtualtrials.com/peacock1.cfm.

Gu et al. GPU-based ultra-fast dose calculation using a finite size pencil beam model. Physics in Medicine and Biology. Oct. 1, 2009, vol. 54, No. 20, pp. 6287-6297.

MacKie, T. Rockwell et al., "Tomotherapy: Rethinking the Processes of Radiotherapy," XIIth ICCR, May 27-30, 1997.

Fang, Guang Y. et al., "Software system for the UW/GE tomotherapy prototype," XIIth ICCR, May 27-30, 1997.

PCT/US2009/062075 International Search Report and Written Opinion dated May 28, 2010.

Office Action from Chinese Patent Office for Application No. 200880110975.2 dated Aug. 5, 2011.

Office Action from Chinese Patent Office for Application No. 200880110975.2 dated Mar. 2, 2012.

Office Action from U.S. Patent and Trademark Office for U.S. Appl. No. 12/259,038 dated Jul. 13, 2011.

Office Action from U.S. Patent and Trademark Office for U.S. Appl. No. 12/259,038 dated Nov. 8, 2012.

Office Action from Japanese Patent Office for Application No. 2010-531317 dated Feb. 6, 2013.

* cited by examiner

SYSTEM AND METHOD FOR MOTION ADAPTIVE OPTIMIZATION FOR RADIATION THERAPY DELIVERY

RELATED APPLICATIONS

This application claims priority to U.S. Provisional Patent Application No. 61/034,009, filed on Mar. 5, 2008, titled REAL TIME ADAPTIVE THERAPY, and is a continuation-in-part of U.S. patent application Ser. No. 12/259,038, filed on Oct. 27, 2008, titled SYSTEM AND METHOD FOR MOTION ADAPTIVE OPTIMIZATION FOR RADIATION THERAPY DELIVERY, the entire contents of both of which are incorporated herein by reference.

BACKGROUND OF THE INVENTION

It is common knowledge that tumors move during and in-between delivery of radiation therapy treatments (Webb, 2006a, Langen and Jones, 2001). The reported real-time motion compensation methods are mainly tracking-based. That is, compensation is done effectively by putting the same intensity of radiation beam on the same position in the tumor reference frame at the same time as what was planned. These methods are implemented through linac tracking (Nuyttens et al., 2006, Murphy, 2004), MLC tracking (Keall et al., 2001, Keall et al., 2006, Neicu et al., 2003) or couch tracking (D'Souza et al., 2005), and can be characterized as hardware solutions.

Papiez et al. (Papiez et al., 2005, Papiez and Rangaraj, 2005, Papiez et al., 2007, Papiez et al., 1999, Papiez and Timmerman, 2008, Papiez et al., 1994, Papiez and Langer, 2006, Papiez et al., 2002, Papieza, 2004), McMahon et al. (McMahon et al., 2007a, McMahon et al., 2007b) and Webb et al. (Webb and Binnie, 2006, Webb, 2006b) incorporated the tumor motion into the dynamic MLC leaf velocity optimization. These methods are considered software approaches to motion compensation.

Tracking-based methods intend to fully and instantly compensate motion errors once motion is detected. Such schemes are considered open-loop methods because they do not explicitly model the compensation errors from hardware limitations and/or prediction. These open-loop tracking methods put great demands on hardware such as the velocity and position accuracy of the MLC, linac or the couch etc., as well as on the accuracy of motion prediction.

SUMMARY OF THE INVENTION

State-of-the-art intensity modulated radiation therapy ("IMRT") delivery follows a planned leaf sequence. The leaf sequence is optimized during treatment planning, which assumes a certain treatment configuration, including patient setup, anatomy and the physiological state. However, it is difficult to accurately model real-time treatment configurations, e.g., patient respiration, during the treatment planning procedure. The deviation of treatment delivery conditions from planning conditions results in sub-optimal dose distributions. In particular, IMRT delivery, which is dynamic in nature, on moving tumors could have the consequence of hot and cold spots across the tumor volume.

Accurate modeling or even long term prediction of tumor motion is still an infeasible task due to the complexity of intra-fraction motion, which is not only patient-specific but also varies from second to second for the same patient. However, real-time motion compensation is promising because it does not rely much on the a priori knowledge or assumption about intra-fraction motion.

The present invention includes a closed loop feedback system of IMRT delivery that incorporates real-time optimization to account for cumulative errors and to accommodate future irradiation. A feasible workflow of real-time motion-adaptive-optimization ("MAO") for radiation therapy delivery has been developed.

Radiation therapy delivery is characterized by many projections. The MAO guided delivery updates the motion-encoded cumulative dose and optimizes the leaf sequence right before the delivery of each projection. The MAO technique includes several real-time procedures including motion detection and prediction, delivered dose accumulation, future dose estimation, and projection optimization. When MAO is performed in real-time, these procedures are to be executed in less than one projection of time. Testing of these MAO procedures took less than 100 ms.

The MAO guided delivery was compared with two other types of delivery, motion-without-compensation delivery (MD) and static delivery (SD), using simulated 1D cases, real treatment plans, and the motion traces from clinical lung and prostate patients. The results show that the proposed MAO technique effectively compensated for motion errors for all test cases. Dose distributions and DVHs of MAO guided delivery approach those of SD very well, whether the motion is regular or irregular respiration, or small or large prostate motion.

Those results conceptually proved the proposed method is applicable for real-time motion compensation in radiation therapy delivery. The method of real-time optimization can be applied to Adaptive Radiation Therapy (ART) to compensate for all kinds of delivery errors.

In one embodiment, the invention provides a method of delivering a radiation therapy treatment. The method includes generating a treatment plan for a patient and positioning the patient to receive radiation. Machine parameters are monitored in substantially real-time. Monitoring the machine parameters includes analyzing information regarding the machine parameters and how the parameters affect dose delivered to the patient. At least a portion of the treatment plan is optimized in substantially real-time to incorporate the analyzed information from the monitored machine parameters. The method further includes delivering at least a portion of the optimized treatment plan to the patient.

Other aspects of the invention will become apparent by consideration of the detailed description and accompanying drawings.

DETAILED DESCRIPTION

Figure 1:
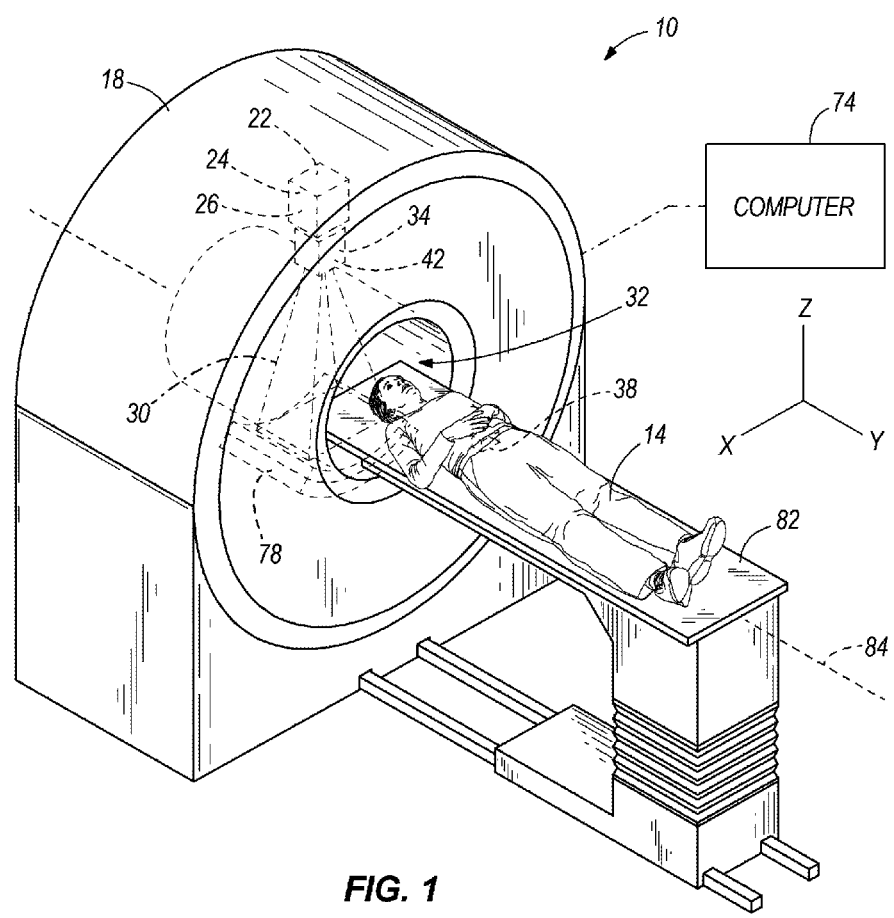
FIG. 1 is a perspective view of a radiation therapy treatment system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

In addition, it should be understood that embodiments of the invention include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a radiation therapy treatment system 10 that can provide radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a gantry 18. The gantry 18 can support a radiation module 22, which can include a radiation source 24 and a linear accelerator 26 (a.k.a. "a linac") operable to generate a beam 30 of radiation. Though the gantry 18 shown in the drawings is a ring gantry, i.e., it extends through a full 360° arc to create a complete ring or circle, other types of mounting arrangements may also be employed. For example, a C-type, partial ring gantry, or robotic arm could be used. Any other framework capable of positioning the radiation module 22 at various rotational and/or axial positions relative to the patient 14 may also be employed. In addition, the radiation source 24 may travel in path that does not follow the shape of the gantry 18. For example, the radiation source 24 may travel in a non-circular path even though the illustrated gantry 18 is generally circular-shaped. The gantry 18 of the illustrated embodiment defines a gantry aperture 32 into which the patient 14 moves during treatment.

The radiation module 22 can also include a modulation device 34 operable to modify or modulate the radiation beam 30. The modulation device 34 provides the modulation of the radiation beam 30 and directs the radiation beam 30 toward the patient 14. Specifically, the radiation beam 30 is directed toward a portion 38 of the patient. Broadly speaking, the portion may include the entire body, but is generally smaller than the entire body and can be defined by a two-dimensional area and/or a three-dimensional volume. A portion or area desired to receive the radiation, which may be referred to as a target or target region, is an example of a region of interest. Another type of region of interest is a region at risk. If a portion includes a region at risk, the radiation beam is preferably diverted from the region at risk. Such modulation is sometimes referred to as intensity modulated radiation therapy ("IMRT").

Figure 2:
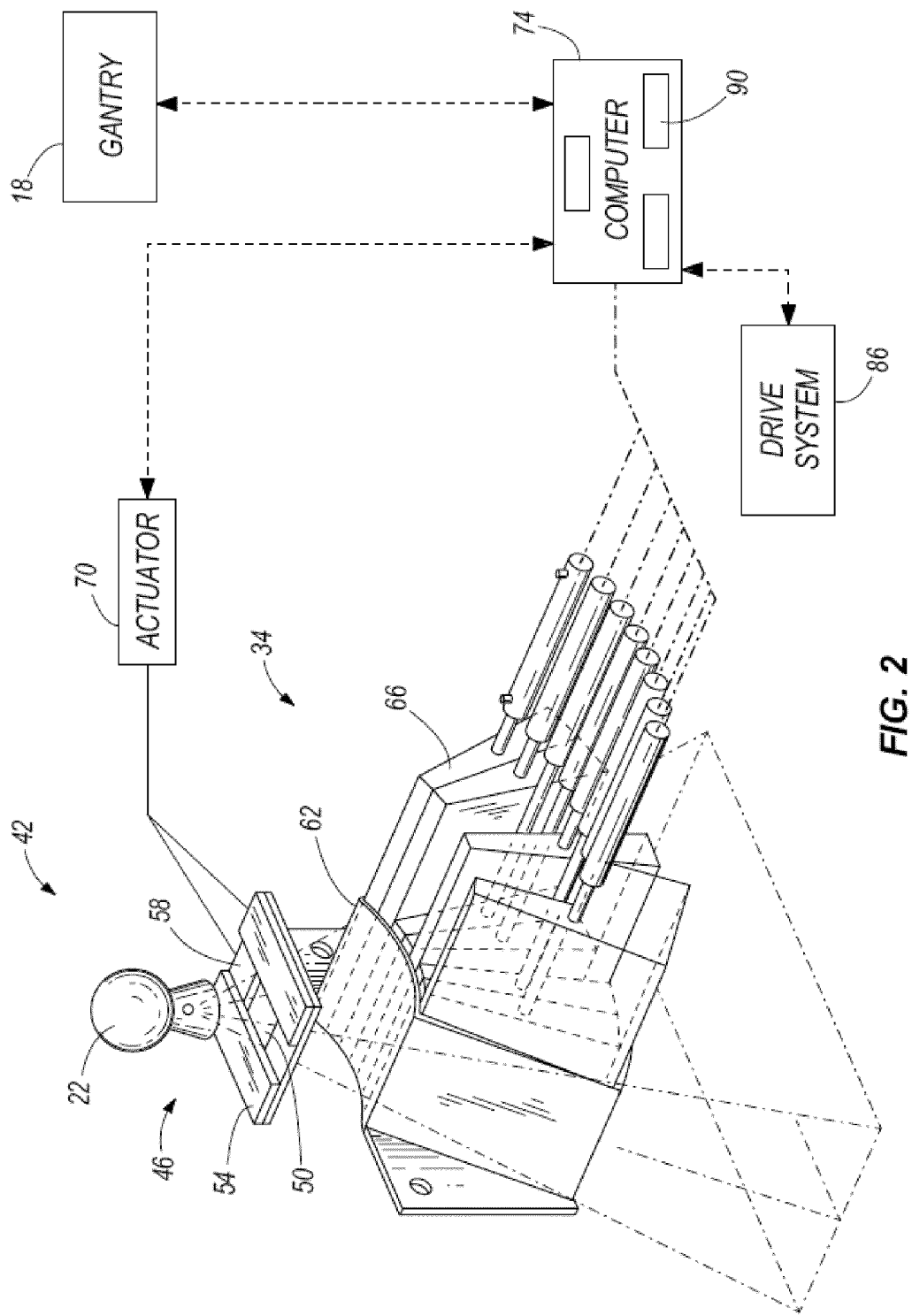
FIG. 2 is a perspective view of a multi-leaf collimator that can be used in the radiation therapy treatment system illustrated in FIG. 1.

The modulation device 34 can include a collimation device 42 as illustrated in FIG. 2. The collimation device 42 includes a set of jaws 46 that define and adjust the size of an aperture 50 through which the radiation beam 30 may pass. The jaws 46 include an upper jaw 54 and a lower jaw 58. The upper jaw 54 and the lower jaw 58 are moveable to adjust the size of the aperture 50. The position of the jaws 46 regulates the shape of the beam 30 that is delivered to the patient 14.

In one embodiment, and illustrated in FIG. 2, the modulation device 34 can comprise a multi-leaf collimator 62 (a.k.a. "MLC"), which includes a plurality of interlaced leaves 66 operable to move from position to position, to provide intensity modulation. It is also noted that the leaves 66 can be moved to a position anywhere between a minimally and maximally-open position. The plurality of interlaced leaves 66 modulate the strength, size, and shape of the radiation beam 30 before the radiation beam 30 reaches the portion 38 on the patient 14. Each of the leaves 66 is independently controlled by an actuator 70, such as a motor or an air valve so that the leaf 66 can open and close quickly to permit or block the passage of radiation. The actuators 70 can be controlled by a computer 74 and/or controller.

The radiation therapy treatment system 10 can also include a detector 78, e.g., a kilovoltage or a megavoltage detector, operable to receive the radiation beam 30, as illustrated in FIG. 1. The linear accelerator 26 and the detector 78 can also operate as a computed tomography (CT) system to generate CT images of the patient 14. The linear accelerator 26 emits the radiation beam 30 toward the portion 38 in the patient 14. The portion 38 absorbs some of the radiation. The detector 78 detects or measures the amount of radiation absorbed by the portion 38. The detector 78 collects the absorption data from different angles as the linear accelerator 26 rotates around and emits radiation toward the patient 14. The collected absorption data is transmitted to the computer 74 to process the absorption data and to generate images of the patient's body tissues and organs. The images can also illustrate bone, soft tissues, and blood vessels. The system 10 can also include a patient support device, shown as a couch 82, operable to support at least a portion of the patient 14 during treatment. While the illustrated couch 82 is designed to support the entire body of the patient 14, in other embodiments of the invention the patient support need not support the entire body, but rather can be designed to support only a portion of the patient 14 during treatment. The couch 82 moves into and out of the field of radiation along an axis 84 (i.e., Y axis). The couch 82 is also capable of moving along the X and Z axes as illustrated in FIG. 1.

Figure 3:
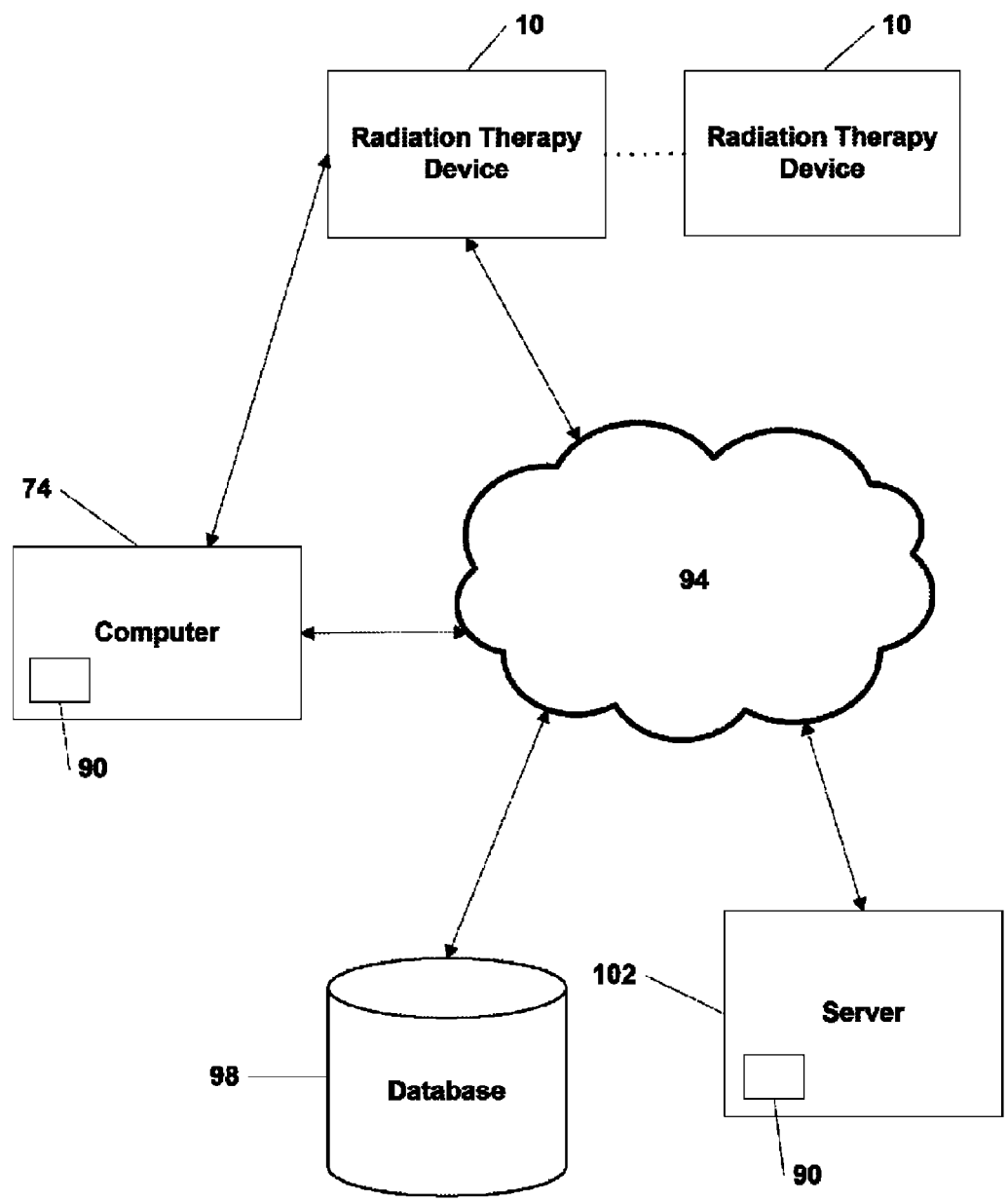
FIG. 3 is a schematic illustration of the radiation therapy treatment system of FIG. 1.

The computer 74, illustrated in FIGS. 2 and 3, includes an operating system for running various software programs and/or a communications application. In particular, the computer 74 can include a software program(s) 90 that operates to communicate with the radiation therapy treatment system 10. The computer 74 can include any suitable input/output device adapted to be accessed by medical personnel. The computer 74 can include typical hardware such as a processor, I/O interfaces, and storage devices or memory. The computer 74 can also include input devices such as a keyboard and a mouse. The computer 74 can further include standard output devices, such as a monitor. In addition, the computer 74 can include peripherals, such as a printer and a scanner.

The computer 74 can be networked with other computers 74 and radiation therapy treatment systems 10. The other computers 74 may include additional and/or different computer programs and software and are not required to be identical to the computer 74, described herein. The computers 74 and radiation therapy treatment system 10 can communicate with a network 94. The computers 74 and radiation therapy treatment systems 10 can also communicate with a database(s) 98 and a server(s) 102. It is noted that the software program(s) 90 could also reside on the server(s) 102.

The network 94 can be built according to any networking technology or topology or combinations of technologies and topologies and can include multiple sub-networks. Connections between the computers and systems shown in FIG. 3 can be made through local area networks ("LANs"), wide area networks ("WANs"), public switched telephone networks ("PSTNs"), wireless networks, Intranets, the Internet, or any other suitable networks. In a hospital or medical care facility, communication between the computers and systems shown in FIG. 3 can be made through the Health Level Seven ("HL7") protocol or other protocols with any version and/or other required protocol. HL7 is a standard protocol which specifies the implementation of interfaces between two computer applications (sender and receiver) from different vendors for electronic data exchange in health care environments. HL7 can allow health care institutions to exchange key sets of data from different application systems. Specifically, HL7 can define the data to be exchanged, the timing of the interchange, and the communication of errors to the application. The formats are generally generic in nature and can be configured to meet the needs of the applications involved.

Communication between the computers and systems shown in FIG. 3 can also occur through the Digital Imaging and Communications in Medicine (DICOM) protocol with any version and/or other required protocol. DICOM is an international communications standard developed by NEMA that defines the format used to transfer medical image-related data between different pieces of medical equipment. DICOM RT refers to the standards that are specific to radiation therapy data.

The two-way arrows in FIG. 3 generally represent two-way communication and information transfer between the network 94 and any one of the computers 74 and the systems 10 shown in FIG. 3. However, for some medical and computerized equipment, only one-way communication and information transfer may be necessary.

Figure 4:
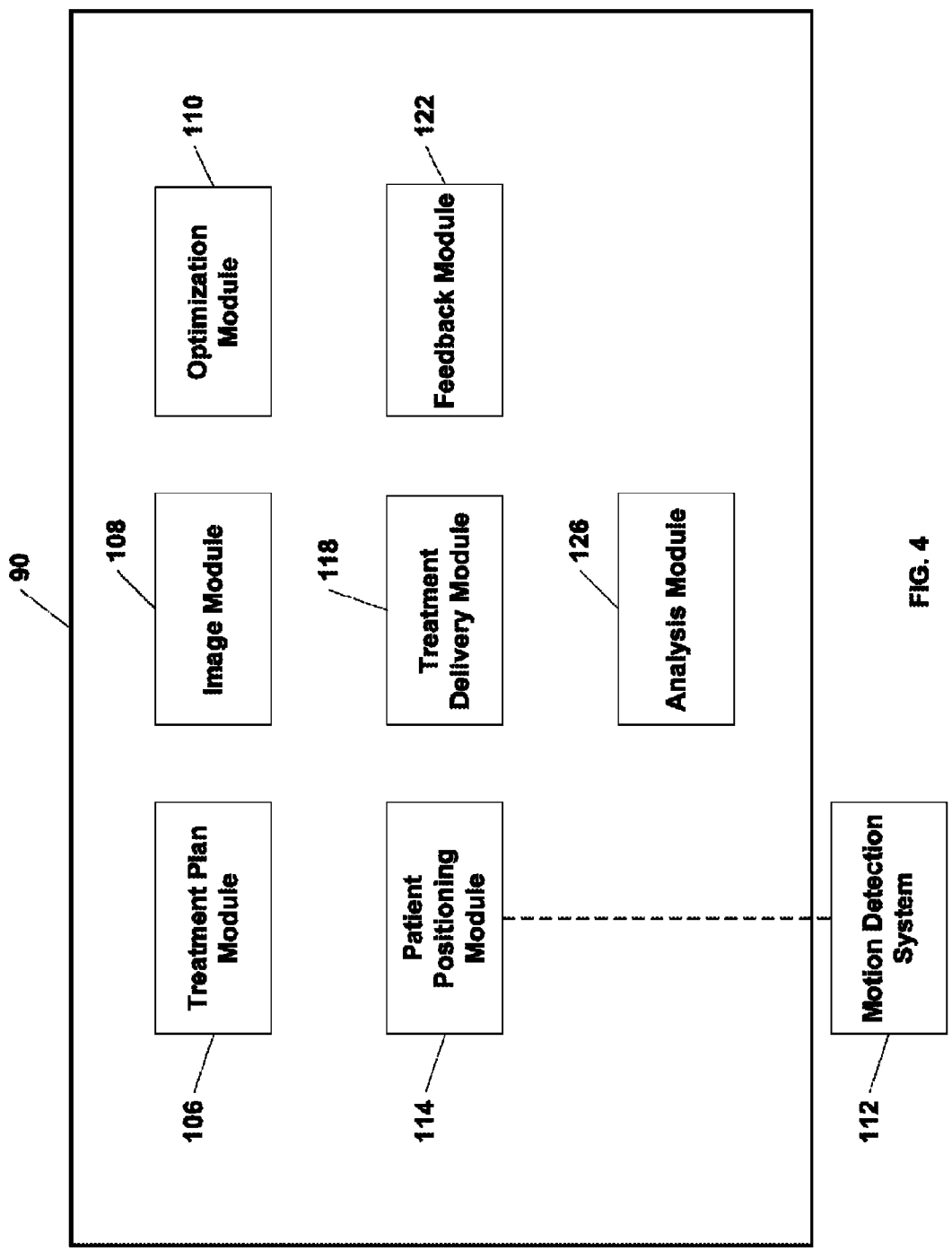
FIG. 4 is a schematic diagram of a software program used in the radiation therapy treatment system.

The software program 90 (illustrated in block diagram form in FIG. 4) includes a plurality of modules that communicate with one another to perform functions of the radiation therapy treatment process. The various modules also communicate with one another to determine if delivery of the radiation therapy treatment plan occurred as intended.

The software program 90 includes a treatment plan module 106 operable to generate a treatment plan for the patient 14 based on data input to the system 10 by medical personnel. The data includes one or more images (e.g., planning images and/or pre-treatment images) of at least a portion of the patient 14. The treatment plan module 106 separates the treatment into a plurality of fractions and determines the radiation dose for each fraction or treatment based on the prescription input by medical personnel. The treatment plan module 106 also determines the radiation dose for the portion 38. The radiation dose can be based on various contours drawn around the portion 38 that define the margin around the portion 38. Multiple portions 38 may be present and included in the same treatment plan.

The treatment plan includes a plurality of projections in which radiation is delivered to the patient. The treatment plan module 106 also is operable to define a time period for each of the projections. The treatment plan module 106 can adjust the time periods for each projection beyond a total time period of all of the projections to build in a buffer for delivering the treatment plan. In other words, the treatment plan module 106 can intentionally under-utilize a delivery capacity to enable more re-optimization opportunities.

The software program 90 also includes an image module 108 operable to acquire images of at least a portion of the patient 14. The image module 108 can instruct the on-board image device, such as a CT imaging device to acquire images of the patient 14 before treatment commences, during treatment, and after treatment according to desired protocols. In one aspect, the image module 108 acquires an image of the patient 14 while the patient 14 is substantially in a treatment position. Other off-line imaging devices or systems may be used to acquire pre-treatment images of the patient 14, such as non-quantitative CT, MRI, PET, SPECT, ultrasound, transmission imaging, fluoroscopy, RF-based localization, and the like. The acquired pre-treatment image(s) can be used for registration of the patient 14 and/or to generate a deformation map to identify the differences between one or more of the planning images and one or more of the pre-treatment, during-treatment, or after-treatment images.

The acquired images also can be used for registration of the patient 14 and/or to determine or predict a radiation dose to be delivered to the patient 14. The acquired images also can be used to determine a radiation dose that the patient 14 received during prior treatments or fractions. The image module 108 also is operable to acquire images of at least a portion of the patient 14 while the patient is receiving treatment to determine a radiation dose that the patient 14 is receiving in real-time.

The software program 90 also includes an optimization module 110 operable to optimize the treatment plan prior to and during treatment delivery. Optimization in real-time during treatment delivery can better take into account a variety of factors, such as patient anatomical and physiological changes (e.g., respiration and other movement, etc.), and machine configuration changes (e.g., beam output factors, couch error, leaf error, etc.). Real time modification of the beam intensity can account for these changes (e.g., re-optimize beamlets in real time).

The optimization module 110 accounts for cumulative errors and to adjust the treatment plan for future irradiation delivered to the patient. The optimization module 110 updates the motion-encoded cumulative dose and optimizes the leaf open time right before the delivery of each projection. Additional details on the optimization of a treatment plan are discussed below.

The software program 90 also includes a patient positioning module 114 operable to position and align the patient 14 with respect to the isocenter of the gantry 18 for a particular treatment fraction. While the patient is on the couch 82, the patient positioning module 114 acquires an image of the patient 14 and compares the current position of the patient 14 to the position of the patient in a reference image. The reference image can be a planning image, any pre-treatment image, or a combination of a planning image and a pre-treatment image. If the patient's position needs to be adjusted, the patient positioning module 114 provides instructions to the drive system 86 to move the couch 82 or the patient 14 can be manually moved to the new position. In one construction, the patient positioning module 114 can receive data from lasers positioned in the treatment room to provide patient position data with respect to the isocenter of the gantry 18. Based on the data from the lasers, the patient positioning module 114 provides instructions to the drive system 86, which moves the couch 82 to achieve proper alignment of the patient 14 with respect to the gantry 18. It is noted that devices and systems, other than lasers, can be used to provide data to the patient positioning module 114 to assist in the alignment process.

The patient positioning module 114 also is operable to detect and/or monitor patient motion during treatment. The patient positioning module 114 may communicate with and/or incorporate a motion detection system 112, such as x-ray, in-room CT, laser positioning devices, camera systems, spirometers, ultrasound, tensile measurements, chest bands, and the like. The patient motion can be irregular or unexpected, and does not need to follow a smooth or reproducible path.

The software program 90 also includes a treatment delivery module 118 operable to instruct the radiation therapy treatment system 10 to deliver the fraction to the patient 14 according to the treatment plan. The treatment delivery module 118 can generate and transmit instructions to the gantry 18, the linear accelerator 26, the modulation device 34, and the drive system 86 to deliver radiation to the patient 14. The instructions coordinate the necessary movements of the gantry 18, the modulation device 34, and the drive system 86 to deliver the radiation beam 30 to the proper target in the proper amount as specified in the treatment plan.

The treatment delivery module 118 also calculates the appropriate pattern, position, and intensity of the radiation beam 30 to be delivered, to match the prescription as specified by the treatment plan. The pattern of the radiation beam 30 is generated by the modulation device 34, and more particularly by movement of the plurality of leaves in the multi-leaf collimator. The treatment delivery module 118 can utilize canonical, predetermined or template leaf patterns to generate the appropriate pattern for the radiation beam 30 based on the treatment parameters. The treatment delivery module 118 can also include a library of patterns for typical cases that can be accessed in which to compare the present patient data to determine the pattern for the radiation beam 30.

The software program 90 also includes a feedback module 122 operable to receive data from the radiation therapy treatment system 10 during a patient treatment. The feedback module 122 can receive data from the radiation therapy treatment device and can include information related to patient transmission data, ion chamber data, MLC data, system temperatures, component speeds and/or positions, flow rates, etc. The feedback module 122 can also receive data related to the treatment parameters, amount of radiation dose the patient received, image data acquired during the treatment, and patient movement. In addition, the feedback module 122 can receive input data from a user and/or other sources. The feedback module 122 acquires and stores the data until needed for further processing.

The software program 90 also includes an analysis module 126 operable to analyze the data from the feedback module 122 to determine whether delivery of the treatment plan occurred as intended and to validate that the planned delivery is reasonable based on the newly-acquired data. The analysis module 126 can also determine, based on the received data and/or additional inputted data, whether a problem has occurred during delivery of the treatment plan. For example, the analysis module 126 can determine if the problem is related to an error of the radiation therapy treatment device 10, an anatomical error, such as patient movement, and/or a clinical error, such as a data input error. The analysis module 126 can detect errors in the radiation therapy treatment device 10 related to the couch 82, the device output (i.e., linear accelerator 26 output variations), the gantry 18, the multi-leaf collimator 62, the patient setup, and timing errors between the components of the radiation therapy treatment device 10. For example, the analysis module 126 can determine if a couch replacement was performed during planning, if fixation devices were properly used and accounted for during planning, if position and speed is correct during treatment. The analysis module 126 can determine whether changes or variations occurred in the output parameters of the radiation therapy treatment device 10. With respect to the gantry 18, the analysis module 126 can determine if there are errors in the speed and positioning of the gantry 18. The analysis module 126 can receive data to determine if the multi-leaf collimator 62 is operating properly. For example, the analysis module 126 can determine if the leaves 66 move at the correct times, if any leaves 66 are stuck in place, if leaf timing is properly calibrated, and whether the leaf modulation pattern is correct for any given treatment plan. The analysis module 126 also can validate patient setup, orientation, and position for any given treatment plan. The analysis module 126 also can validate that the timing between the gantry 18, the couch 62, the linear accelerator 26, the leaves 66 are correct.

The analysis module 126 can also utilize deformable registration data to ensure that the patient 14 is receiving the correct radiation dose across multiple fractions. When analyzing the doses, it is useful to accumulate the dose across multiple treatment fractions to determine if any errors are being exacerbated or if they are mitigating each other. Registration is a method for determining the correlation between locations of a patient's anatomy or physiology across multiple images. Deformable registration is a method of determining the correlation between locations of a patient's anatomy or physiology to account for non-rigid changes in anatomy between the images, phases, or times. The radiation dose delivered to the patient 14 is recalculated based upon on-line images and feedback from the radiation therapy treatment device 10 to ensure that the correct dose has been or is being delivered to the patient 14.

The analysis module 126 also can utilize data related to deformation-based contouring of images for quality assurance purposes. Deformable registration techniques can be used to generate automatic or semi-automatic contours for new images. Generally, a contour set has been defined for planning or other baseline patient images, but with new images, a contour set is not usually readily available. Rather than require an operator to manually contour the image, it can be both faster and more consistent to perform a deformable image registration, and then use the deformation results as the basis for modifying the original contour set to reflect the new patient anatomy. A similar family of template-based contouring algorithms has been developed to generate contours for newly available images, based upon previously available sets of images and contours. These template-based algorithms might contour a new patient image based upon a previous patient image and contour, or potentially based upon a canonical or atlas patient image and contour. This can be performed for adaptive therapy as a means to accumulate doses in daily images, each with automatic daily contours. Moreover, whereas previously these algorithms were used in the context of generating new contours based upon canonical or atlas images, it is a new aspect of this invention to apply these techniques to the particular wealth of image data and types of images that arise during image-guided radiotherapy. Specifically, this includes deformation and template-based contouring of multiple images of the same patient in which contour sets might only exist for one of the images. These multiple images of the patient may arise from use of an on-line or in-room patient imaging system, with images potentially taken on different days, or these images might derive from a "4D" imaging system such as a CT scanner, in which each image represents a phase of motion, such as a breathing phase. It should also be noted that the on-line or in-room imaging system might be the same, a similar, or a different modality from the reference image. For example, the reference image might be a CT image, whereas the on-line image could be CT, cone-beam CT, megavoltage CT, MRI, ultrasound, or a different modality. By porting these contouring techniques to the applications of quality assurance and adaptive therapy, it is possible to both save a considerable amount of time from the contouring of images, and this method can also improve the consistency of contours across multiple images of the same patient (taken at different times or representing different phases). It is known that manual contours can suffer from irreproducibility, whereas automatically generated contours can potentially be more consistent in applying the principles of an initial contour to the generation of subsequent contours.

Another benefit of the contouring process using deformable registration techniques is that the contours generated can provide a validation of the deformation process. If the generated contours closely reflect contours that one would manually draw, then it is a good indication that the deformation process is reasonable; whereas if the automatic contours are less relevant, it indicates to the user that perhaps the deformation is inappropriate, but also provides the user an opportunity to verify the manual contours to check for mistakes or inconsistencies. Another aspect of this method is that the deformation-based contours can be used as a rough-draft of the contours for the adaptive process, and manually edited to reflect the desired contours for the on-line images. When doing this, the deformation process can then be re-run, constraining the deformation map to match the initial contours to the manually-edited automatic contours, and this helps direct consistent results through the rest of the image.

The analysis module 126 also is operable to utilize deformation maps to perform dose calculations on various images for quality assurance purposes. A deformation map can be utilized to relate a plurality of images where one image is a planning image that is useful for dose calculation, and another image, such as an on-line image, has qualitative value but less direct utility for dose calculation. This relation could then be used to "remap" the more quantitative image to the qualitative shape of the on-line or less quantitative image. The resulting remapped image would be more appropriate than either of the other two images for dose calculation or quantitative applications as it would have the quantitative benefits of the first image, but with the updated anatomical information as contained in the second image. This could be useful in a variety of cases, such as where the first image (e.g., a planning image) is a CT and where the additional image lacks quantitative image values (e.g., MRI, PET, SPECT, ultrasound, or non-quantitative CT, etc. images). A similar application of this method would be to correct for geometrical distortion, imperfections, and/or incompleteness in lieu of, or in addition to, quantitative limitations. For example, a current MRI image that well represents anatomy but includes geometric distortion might be remapped to a CT image that is not distorted. Or multiple images could be used to simultaneously correct for both distortion while representing anatomical changes.

As noted above, it is important to be able to recalculate dose on patient images acquired after the planning image. Given these doses, it is also useful to accumulate these doses for multiple delivered fractions. These doses can be added based upon the location of the doses in physical space, but a better method is to incorporate deformation methods into the process so as to add doses based upon the structures that received the dose, even if the structures have changed location. However, it is possible to build upon this technology to perform novel types of adaptive therapy.

In the context of recalculating doses, there are several other aspects of this invention to improve or facilitate this process. For example, after recording any daily registrations applied to the patient, potentially based upon image-guidance, these same registrations can optionally be applied to the patient images when recalculating dose. This can be performed automatically or semi-automatically. Alternately, the dose could be recalculated with a different registration. The benefit is that by automatically using the recorded registrations, the process of recalculating the doses that were delivered is simplified and streamlined. Moreover, by having the ability to recalculate doses for different registrations, one can experiment to determine if other patient alignment protocols might have been more or less effective. And by not using the recorded registration, one can determine how the treatment would have been affected in the absence of image guidance.

The dose recalculation process also can be enhanced by the padding of incomplete images. This is because a limited-size image, whether limited in the axial plane and/or in the superior/inferior direction, can degrade the accuracy of dose calculations. A method to overcome this is to pad the limited-size image with other image data, such as from the planning image. This padding method can work for both axially or superior/inferior limited data. In addition, another method for padding superior/inferior data is to repeat the end slices of the incomplete image as necessary until the data is sufficiently large for improved dose calculation.

Figure 5:
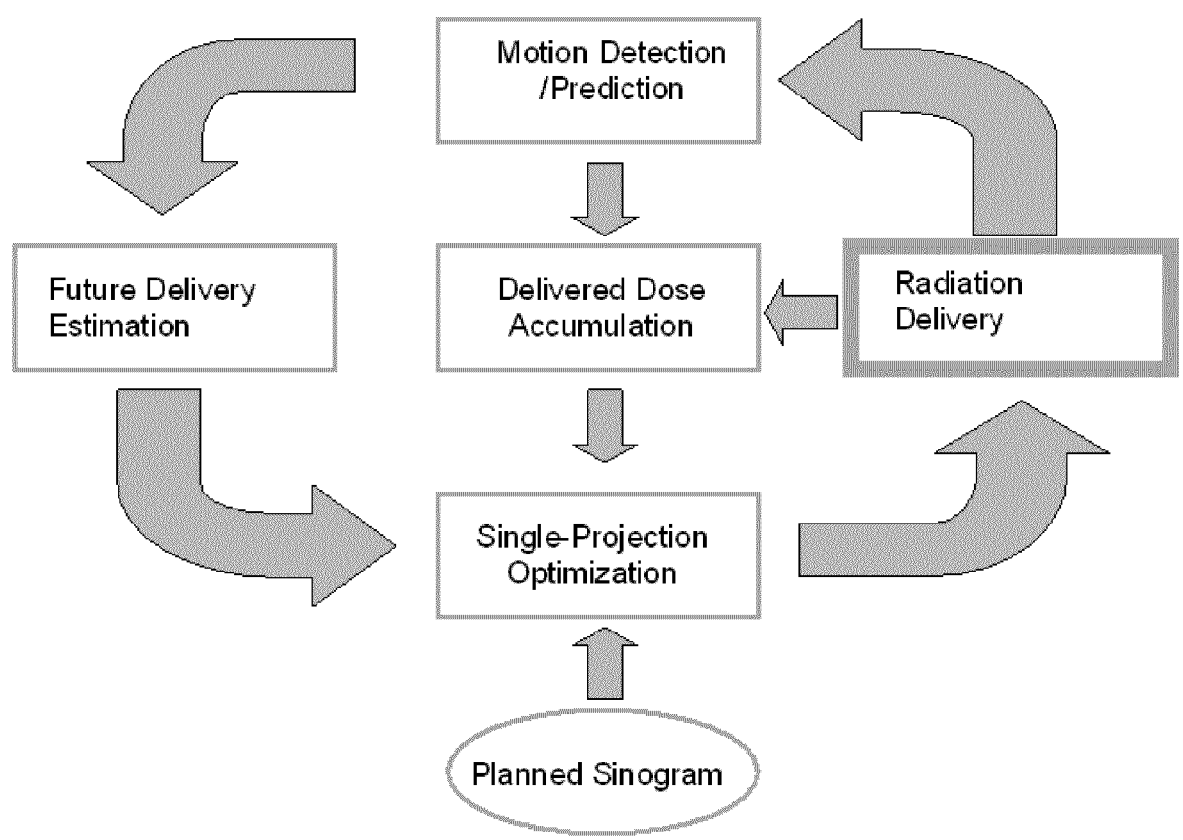
FIG. 5 is a flow chart illustrating real-time MAO-guided radiation therapy delivery
Figure 6:
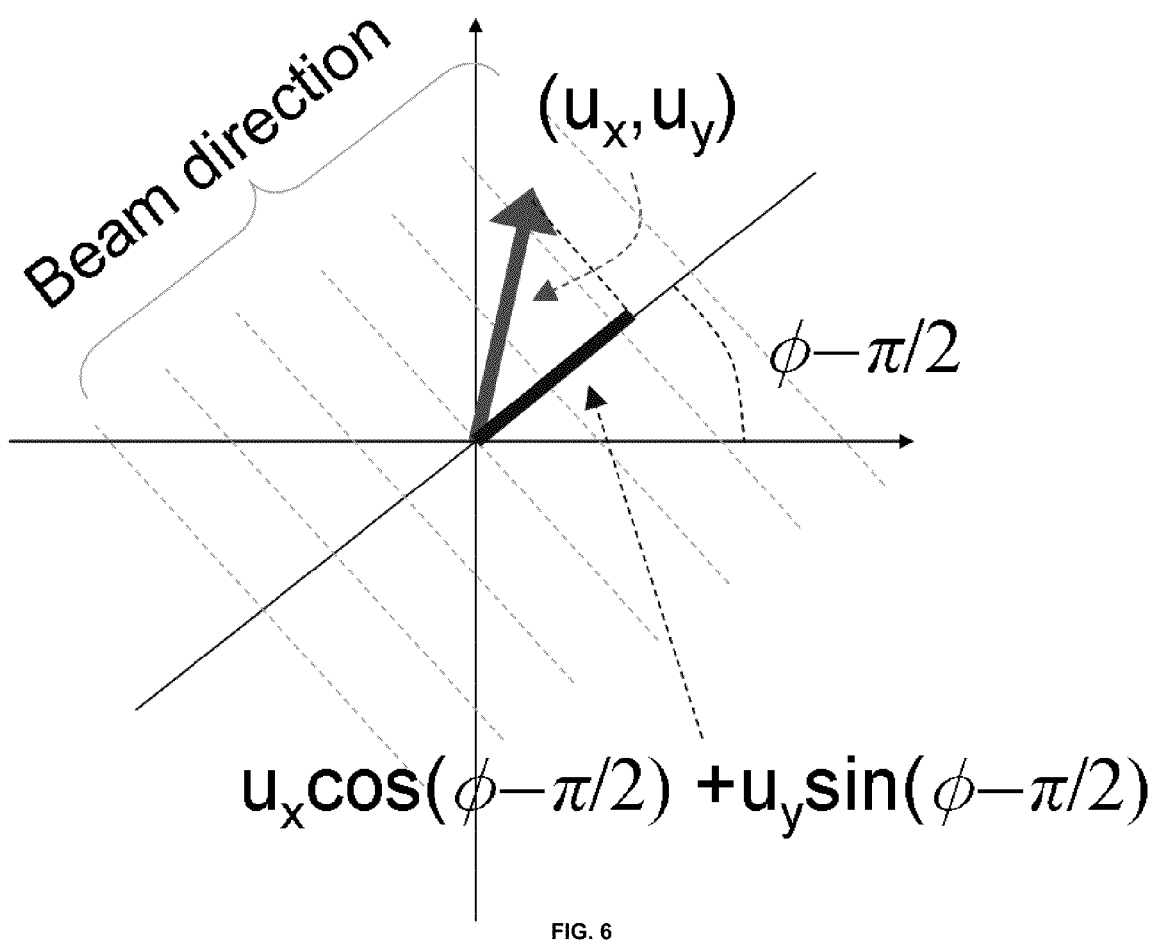
FIG. 6 illustrates a projection of motion u along the leaf direction (cos(φ−π/2), sin(φ−π/2),0), where φ is the angle of source direction.

FIG. 5 illustrates a flow chart for real-time MAO-guided radiation therapy delivery. In this flow chart, a treatment planning system (TPS) is used to optimize a planned sinogram, but no motion margin is added in the planning procedure. This approach does not alter the couch, gantry speed, or jaw positions. In other words, during radiation delivery the couch and the gantry move at constant speed, and the jaws are in fixed positions, just as planned. The tumor position is real-time detected/updated via some surrogates or directly via treatment beams while the motion management system of the present invention is independent of the motion detection methods.

The planned sinogram together with the accumulation of delivered dose, estimation of future dose, and prediction of the tumor position are fed into the optimization process to output the leaf open time for the coming projection. This is considered a closed-loop process because the output of the optimizer is sent to the machine as the instruction to deliver dose, and the delivered dose is real-time accumulated by a 4D dose calculator and sent back (as input) to the optimizer.

The 4D dose calculator is used to accumulate the delivered dose up to the last delivered projection in real-time. The dose to be delivered in future projections (beyond the coming projection) is estimated. Based on the predicted tumor position for the coming projection and accumulated delivered dose, the leaf open time for the coming projection is optimized in real-time to account for both accumulated delivery errors and future dose estimation. The optimized leaf open time is used to control the MLC that modulates the radiation delivery for the coming projection.

This flow chart models the radiation delivery process as a negative feedback system. To implement this flow chart in real-time, the process, as illustrated, except the offline planning procedure, must be executed in less than one projection time. The projection time can be regarded as the temporal resolution of the real-time MAO technique because the system only optimizes once per projection. The minimum projection time for a TomoTherapy® radiation therapy system is about 200 ms, which corresponds to 51 projections per 10 sec gantry rotation.

The following notations will be used throughout this document:

B: matrix of planned beamlet dose of size M×N, where M is the number of voxels and N is the number of beamlets. Each column of B is the dose distribution from a beamlet (leaf) of unit intensity.

w: sinogram of leaf fluence (leaf open time) indexed by the projection number i and the leaf number j, $w=\{w_{i,j}\}$.

$\hat{w}$: planned sinogram obtained through optimization in the planning procedure and emphasized by hat.

$\tilde{w}$: delivery sinogram adjusted from the planned sinogram according to tumor motion and emphasized by tilde.

δ: couch movement per gantry rotation.

P: number of projections per gantry rotation, typically P=51 for the current helical TomoTherapy radiation therapy treatment system.

$u=(u_x, u_y, u_z)$: tumor motion; the upper index in $u^i$ indicates the motion of the i-th projection.

1. Theory 1.1 Plan Optimization

IMRT plan optimization can generally be formulated as a constrained non-linear optimization problem:

$$\hat{w} = \operatorname*{argmin}_{w} F(Bw) \qquad (1)$$

subject to the constraints $$Bw \in D \text{ and } w \in W \qquad (2)$$

where F is the planning objective, D is the space of permissible dose distributions, which satisfy, for example, the minimal and maximal dose and the DVH requirement, and W is the space of feasible fluence maps that are deliverable by hardware of the radiation therapy machine. Typically, the objective function F can be expressed as a weighted sum of multiple objective functions:

$$F = \Sigma_s \alpha_s F_s \qquad (3)$$

Each column in the matrix B of beamlet dose represents a 3D dose distribution for a beamlet of unit intensity and the product Bw is the overall 3D dose distribution as a result of delivering w. The fluence map w can be directly or indirectly converted into delivery instructions for the machine. An example of direct conversion of the fluence map w into delivery instructions is the TomoTherapy® radiation therapy treatment system, where the fluence map describes the leaf open time for every projection. Indirect conversions, like step-and-shoot and dynamic MLC based delivery, convert fluence maps into tens to hundreds of segments or several leaf sequences. IMRT optimization is usually a time consuming process that takes tens of minutes or hours even with state-of-the-art computers. The following are the contributing factors that make IMRT optimization a lengthy process:

1. Different components of the objective function as in Eq. (3) interact and better tradeoffs can be achieved by users adjusting the weights $\alpha_s$. Therefore, it may involve significant user manipulations to drive the optimization towards clinical objectives.

2. It is categorized as a very large scale non-linear optimization problem. The problem size is reflected in the size of the matrix B. The number of unknowns (i.e., number of beamlets, or number of columns in B) can be as large as thousands for conventional IMRT and tens of thousands or even hundreds of thousands for optimization. The number of rows in B corresponds to the number of voxels in the 3D volume, which is typically on the order of millions.

3. The matrix B is quite dense, not sparse. Theoretically, each beamlet has contributions to all voxels in the 3D volume because of scatter. Even if the primary radiation is considered, each voxel is directly irradiated by 51/0.3=170 beamlets, given that there are 51 projections per rotation and a typical pitch of 0.3 in the case of the TomoTherapy® system. That is, the optimizer has to find out tradeoffs among those beamlets to minimize the objective function, and it usually requires hundreds of iterations for results to converge.

To be focused, in the following discussion, we only study the TomoTherapy$^{SM}$ treatment delivery mode. However, it is noted that adaptive techniques could be applied to other radiation delivery devices and systems and to other types of delivery. TomoTherapy$^{SM}$ treatment delivery is projection-wised. That is, the fluence map w is organized into a sinogram of beamlet intensities:

$$w=\{w_{i,j}\} \quad (4)$$

where i is the projection index and j is the leaf index. Typically, there are hundreds to thousands of projections in each sinogram.

1.2 Motion-Encoded Beamlets

A beamlet matrix B, which is associated with a static patient, is pre-calculated off-line before plan optimization. Same as for plan optimization, the beamlet matrix is essential in accumulating dose and updating the fluence map for real-time optimization. But, when the tumor moves during delivery, the radiation source may no longer be at the planned positions in the tumor reference frame. Therefore, the original beamlet matrix B is no longer valid for describing the patient dose distribution and revisions of the beamlet matrix are necessary. We call such revised beamlets motion-encoded beamlets. Re-calculating beamlets from scratch in real-time is infeasible. In the following, approximations of motion-encoded beamlets that are modified from the original beamlets in real-time are described.

Suppose, at the time of delivering the i-th projection, tumor motion is $u=(u_x, u_y, u_z)$. The modification of beamlets can be decomposed into the longitudinal and the transversal directions. Let us first consider the longitudinal direction. For convenience, the source position is referenced to the tumor unless otherwise stated. At the i-th projection, the planned source position is $(i/P)\cdot\delta$, where $\delta$ is couch movement per gantry rotation. With motion $u=(u_x, u_y, u_z)$, the source position changes to $(i/P)\cdot\delta-u_z$. The beamlet of this new source position can be approximated by a linear interpolation of the original beamlets of two nearest projections at the same gantry angle.

$$B'_{i,\cdot}(x)=(1-\alpha)B_{i-mP,\cdot}(x_1)+\alpha B_{i-(m+1)P,\cdot}(x_2) \quad (5)$$

for every point $x=(x, y, z)$ in the space, where $u_z/\delta=m+\alpha$ for some integer m and $0\leq\alpha<1$, and $x_1$ and $x_2$ are defined as $$x_1=(x,y,z+\alpha\delta) \text{ and } x_2=(x,y,z-(1-\alpha)\delta) \quad (6)$$

Similar to longitudinal modification, transversal modification that accounts for transversal motion can also be obtained via linear interpolating the original beamlets of two nearest leaves.

$$\tilde{B}_{i,j}(x)=(1-\beta)B'_{i,j-l}(x_3)+\beta B'_{i,j-l-1}(x_4) \quad (7)$$

where $u_{\phi-\pi/2}/\alpha=l+\beta$ for some integer l and $0\leq\beta<1$, $\alpha$ is the leaf width, $\phi$ is the projection angle, $\phi=(i/P) 2\pi$, and $u_{\phi-\pi/2}$ is the projection of motion u along the leaf direction $(\cos(\phi-\pi/2), \sin(\phi-\pi/2),0)$ as illustrated in FIG. 3. Here, the coordinate shifts $x_3$ and $x_4$ are defined as:

$$x_3=(x,y,z)+\beta\alpha\cdot(\cos(\phi-\pi/2), \sin(\phi-\pi/2),0) \; x_4=(x,y,z)-(1-\beta)\alpha\cdot(\cos(\phi-\pi/2), \sin(\phi-\pi/2),0) \quad (8)$$

Using Eqs. (5) and (7) and assuming the leaf fluence for the i-th projection is $\{w_{i,j}\}$, the motion-encoded dose $d_i$ for the i-th projection should be $$d_i = \sum_j \tilde{B}_{i,j} w_{i,j} \quad (9)$$

1.3 Real-Time MAD

A real-time motion adaptive delivery ("MAD") technique provides an initial guess of fluence and a reasonable model for future dose estimation in the MAO strategy, as will be discussed in later sections. We briefly summarize the MAD technique here.

At any projection, if the tumor motion is $u=(u_x, u_y, u_z)$, which is equivalent to the source moving by $-u$ relative to the tumor from the planned trajectory, then we would use an interpolated leaf open time so that the dose of that projection is closest to what was intended at that position. Let $\hat{w}=\{\hat{w}_{i,j}\}$ denote the planned sinogram where i is the projection index and j is the leaf index. When referenced to the couch, the source position parameterized by the projection index i traces out a helix on a cylindrical surface. If the source is shifted by $-u_z$ in the longitudinal direction for Projection i, then the new leaf fluence $\tilde{w}=\{\tilde{w}_{i,j}(u_z)\}$ can be calculated by linear interpolating the planned sinogram w. That is, $$\tilde{w}_{i,j}(u_z)=(1-\alpha)\cdot\hat{w}_{i-mP,j}+\alpha\cdot\hat{w}_{i-(m+1)P,j} \quad (10)$$

where $u_z/\delta=m+\alpha$ for some integer m and $0\leq\alpha<1$.

The transversal displacement of the source is further compensated for by shifting the leaf fluence with necessary corrections such as the cone effect and the inverse square.

1.4 Real-Time MAO

The time-consuming plan optimization returns an optimal feasible solution $\hat{w}$ so that the dose distribution $d^{plan}=B\hat{w}$ meets the clinician's objectives. However, real-time patient motion is not, or not even possible to be, modeled in the planning procedure. It is expected that the highly conforming planned dose distribution from the hard work of plan optimization will be smeared out due to real-time motion. Real-time MAO guided delivery incorporates optimization into the radiation delivery procedure. In fact, it can be regarded as a negative feedback system that self corrects cumulative errors from previously delivered projections.

Real-time MAO optimizes the leaf open time for only the coming projection. Suppose a planned sinogram includes N projections and immediately before delivery for the nth projection (the coming projection), we want to optimize:

$$\tilde{w}_{n,\cdot} = \underset{w_{n,\cdot}}{\operatorname{argmin}} \| d^{delivery} - d^{plan} \| \quad (11)$$

subject to $$0 \leq w_{n,\cdot} \leq w_{max} \quad (12)$$

where $w_{max}$ is the maximum projection time fixed for each delivery plan, $d^{delivery}$ is defined as $$d^{delivery}=d_-+d_n+d_+ \quad (13)$$

Figure 7:
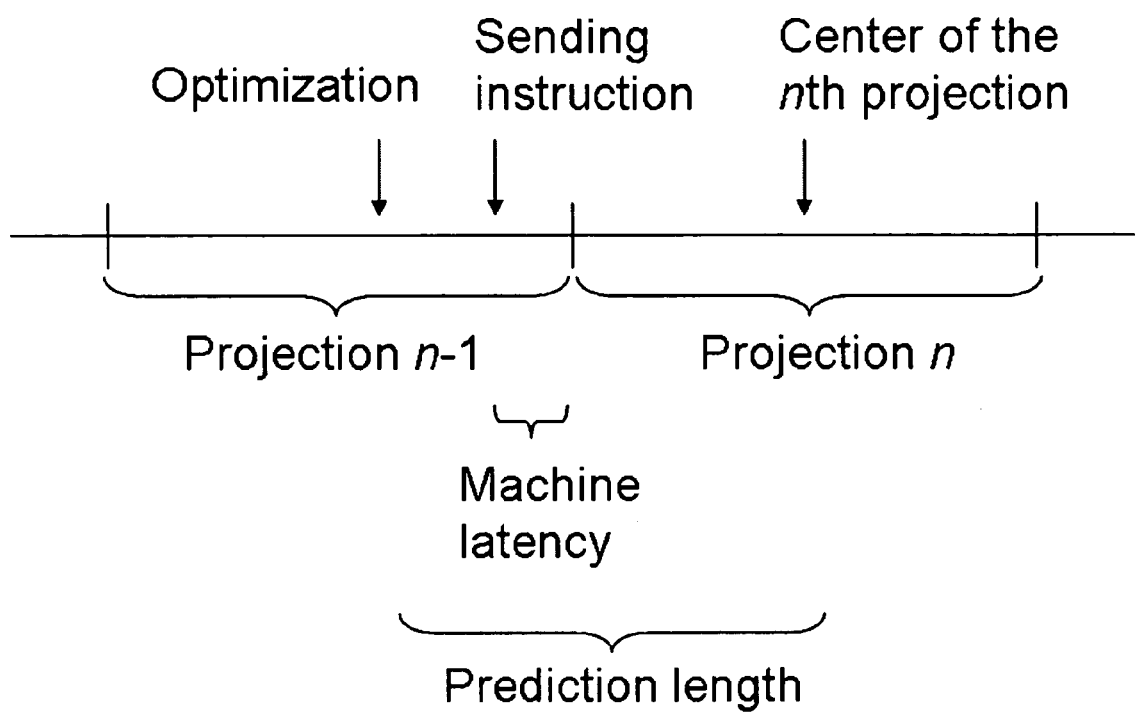
FIG. 7 illustrates a real-time MAO time line. Optimization for the nth projection occurs in the (n−1)-th projection. After optimization is done, the result is sent to the machine for delivery instructions before the nth projection begins.

$d_-$ is the accumulated dose from already delivered projections 1 to n−1, $d_n$ is the dose to be optimized for the n-th projection delivery, and $d_+$ is the future dose to be delivered in projections n+1 to N. Here, dose distributions $d_-$, $d_n$ and $d_+$ are evaluated in the same reference frame as in the planning procedure. FIG. 7 illustrates the time line for the real-time MAO procedures. Optimization for the n-th projection occurs during the delivery of the (n−1)-th projection. The tasks in optimization also include updating the accumulated dose d_ by adding to it last delivered dose of Projection n−1 and estimating future dose d_+ for Projection n+1 to the end.

At the time of optimization, tumor motion is known for Projection n−1, but motion for Projection n needs to be predicted. In the following, we will detail how each task-delivered dose accumulation, future dose estimation and single-projection optimization, is done assuming we are optimizing for the n-th projection.

1.4.1 Delivered Dose Accumulation

Assume we are optimizing for the n-th projection. We have already calculated the accumulated dose d_ for projections 1 to n−2. We need to update the accumulated dose d_ by adding to it last delivered dose of the (n−1)-th projection $d_{n-1}^{delivered}$. We need to know the delivered fluence map $\tilde{w}_{n-1,j}$ and the motion-encoded-beamlets to calculate $d_{n-1}^{delivered}$. The delivered fluence map $\tilde{w}_{n-1,j}$ is just the optimized result for the (n−1)-th projection. However, we only have the planned beamlets which assume no tumor motion. At the time of delivering the (n−1)-th projection, the beamlets are different from the planned ones due to tumor motion $u^{n-1}$. The modification from the planned beamlets to delivery beamlets follows Eqs. (5) and (7). And the dose delivered in Projection n−1 is $$d_{n-1}^{delivered} = \sum_j \tilde{B}_{n-1,j} \tilde{w}_{n-1,j} \qquad (14)$$

and the delivered dose is accumulated simply as:

$$d_- := d_- + d_{n-1}^{delivered} \qquad (15)$$

1.4.2 Future Dose Estimation

Future dose estimation is a tough task because we have two unknowns: 1) tumor motion and 2) the fluence map (leaf open time) for all future projections. If we knew the whole trace of future projections, then the MAD strategy as described above provides a good candidate for future dose estimation. However, in reality, we do not know the whole motion trace beforehand. A natural amendment is to replace motion by its probability density function (PDF) in the MAD strategy and express future dose in terms of expectation. The PDF of motion can be easily estimated based on the previous trace and it is expected that PDF change slowly for future projections. The expected future dose based on the MAD strategy can be pre-calculated off-line.

Step 1: Calculate the planned projection dose $d_i^{plan}(x)$ for every projection i by adding up the contributions from all leaves.

$$d_i^{plan}(x) = \sum_j B_{ij}(x)\hat{w}_{ij} \qquad (16)$$

Step 2: Calculate the cumulated dose $g_0(k, x)$ up to projection k for all k.

$$g_0(k, x) = \sum_{i=1}^{k} d_i^{plan}(x) \qquad (17)$$

In particular, $g_0(N,x)$ denotes the total dose from all projections, where N is the total number of projections.

$$g_0(N, x) = \sum_{i=1}^{N} d_i^{plan}(x) \qquad (18)$$

Step 3: Calculate the cumulated dose $g(k, x, u_z)$ up to Projection k if the source trajectory is shifted by $-u_z$ in the longitudinal direction, which is equivalent to longitudinal tumor motion $u_z$.

$$g(k,x,u_z)=(1-\alpha)g_0(k-mP,x_0)+\alpha g_0(k-(m+1)P,x_1) \qquad (19)$$

where $u_z/\delta=m+\alpha$, $x_0$ and $x_1$ are defined as those in Eq. (6). In particular, we have $$g(N,x,u_z)=(1-\alpha)g_0(N,x_0)+\alpha g_0(N,x_1) \qquad (20)$$

Step 4: Calculate the expectation $\bar{g}(k,x)$ of $g(k, x, u_z)$ with respect to the PDF $p(u_z)$ of motion $u_z$.

$$\bar{g}(k,x)=\int_{\underline{u_z}}^{\overline{u_z}} g(k,x,u_z)p(u_z)du_z \qquad (21)$$

Step 5: Calculate the expected future dose $d_+$.

$$d_+(x)=\bar{g}(N,x)-\bar{g}(n,x) \qquad (22)$$

Our future dose estimation is based on MAD for fluence and PDF of motion.

Because the transversal displacement of the source can be compensated for by shifting the leaf fluence with necessary corrections such as the cone effect and the inverse square, we only need to deal with the longitudinal displacement. As described above, if the source is shifted by $-u_z$ in the longitudinal direction for Projection i, then the new leaf fluence $\tilde{w}=\{\tilde{w}_{i,j}(u_z)\}$ can be calculated by linear interpolating the planned sinogram $\hat{w}$. That is, $$\tilde{w}_{i,j}(u_z)=(1-\alpha)\cdot\hat{w}_{i-mP,j}+\alpha\cdot\hat{w}_{i-(m+1)P,j} \qquad (23)$$

where $u_z/\delta=m+\alpha$ for some integer m and $0\leq\alpha<1$. Similarly, the beamlets can be approximated by linearly interpolating the planned beamlets as in Eq. (5).

$$\tilde{B}_{i,j}(x)=(1-\alpha)B_{i-mP,j}(x')+\alpha B_{i-(m+1)P,j}(x'') \qquad (24)$$

where $x'=(x, y, z+\alpha\delta)$ and $x''=(x, y, z-(1-\alpha)\delta)$. Therefore the new dose for Projection i is $$\begin{aligned}\tilde{d}_i(x) &= \sum_j \tilde{B}_{i,j}(x)\tilde{w}_{i,j} \\ &= (1-\alpha)\cdot\sum_j \tilde{B}_{i,j}(x)\hat{w}_{i-mP,j} + \alpha\cdot\sum_j \tilde{B}_{i,j}(x)\hat{w}_{i-(m+1)P,j} \\ &\approx (1-\alpha)d_{i-mP}(x') + \alpha\cdot d_{i-(m+1)P}(x'')\end{aligned} \qquad (25)$$

Note the third line in Eq. (25) uses the approximations $B_{i,j}(x)\approx B_{i-mP,j}(x')$ and $\tilde{B}_{i,j}(x)\approx B_{i-(m+1)P,j}(x'')$. The new dose $\tilde{d}_i(x)$ is in fact a function of tumor motion. Let us use $\tilde{d}_i(u_z^i, x)$ to denote its dependency on the tumor motion $u_z^i$ of the i-th projection. If motion for future projections is known, then future dose after Projection n can be calculated as $$D_+(x) = \sum_{i=n+1}^{N} \tilde{d}_i(u_z^i, x) \qquad (26)$$

However, motion for future projections is not known in real life. Assuming the PDF's of $u_z^i$ are available and the same for all i>n, denoted by $p(u_z)$, then future dose can be estimated using the expectation of Eq. (26).

$$d_+(x) = \langle D_+(x) \rangle \quad (27)$$
$$= \left\langle \sum_{i=n+1}^{N} \tilde{d}_i(u_z^i, x) \right\rangle$$
$$= \langle g(N, x, u_z) - g(n, x, u_z) \rangle$$
$$= \bar{g}(N, x) - \bar{g}(n, x)$$

where $g$ and $\bar{g}$ are defined above.

1.4.3 Single Projection Optimization

Now that we have calculated $d_-$ and $d_+$, we are ready to optimize the n-th projection. The dose of Projection n is calculated as:

$$d_n = \sum_j \tilde{B}_{n,j} w_{n,j} \quad (28)$$

where $\tilde{B}_{n,j}$ is the motion-encoded beamlet given in Eqs. (5) and (7), where the tumor motion $u^n$ is obtained from prediction based on the motion trace from Projection 1 to n−1 and to be described in the next section. $w_{n,\cdot}$ is the leaf open time to be optimized. There are typically less than 20 active leaves involved in this optimization. Beamlet dose of those leaves have very little overlap, because they are in the same projection. The desired dose distribution $\tilde{d}_n$ according to Eqs. (11) and (13) is $$\tilde{d}_n = \max(d^{plan} - (d_- + d_+), 0) \quad (29)$$

If the beamlets do not overlap, then the fluence map $\tilde{w}_{n,\cdot} = \{\tilde{w}_{n,j}\}$ can be solved in one step.

$$\tilde{d}_n = \sum_j \tilde{B}_{n,j} \tilde{w}_{n,j} \Rightarrow \tilde{w}_{n,j} = \frac{\langle \tilde{B}_{n,j}, \tilde{d}_{n,j} \rangle}{\langle \tilde{B}_{n,j}, \tilde{B}_{n,j} \rangle} \quad (30)$$

Note that $\langle \tilde{B}_{n,j}, \tilde{B}_{n,j'} \rangle = 0$ for $j \neq j'$ because they do no overlap. Here, $\langle , \rangle$ denotes the inner product of two vectors. However, because of radiation penumbra and scatter, we found that the following ratio updating scheme from the k-th to (k+1)-th iteration is more robust:

$$w_{n,j}^{(k+1)} = r_{n,j}^{(k)} w_{n,j}^{(k)} \quad (31)$$

where $$r_{n,j}^{(k)} = \frac{\langle d^{plan}, \tilde{B}_{n,j} \rangle}{\langle d_{(k)}^{delivery}, \tilde{B}_{n,j} \rangle} \quad (32)$$

The fluence obtained from the MAD approach is used as the initial guess $w_{n,\cdot}^{(0)}$. And we set $w_{n,j}$ equal to $w_{max}$ if it exceeds $w_{max}$ to ensure feasible leaf open time. Typically, the optimization converges within 10 iterations.

1.5 Motion Prediction

For any real-time reaction system, prediction is needed because of latency between detection and action. In the case of real-time MAO for TomoTherapy$^{SM}$ treatment, the total latency consists of the time from motion detection to MAO calculation, to sending delivery instruction, to the actual delivery. Such motion may include direct motion, such as respiratory motion or breathing phases, cardiac motion, or other patient motion that causes motion of the tumor from its expected position, or more indirect motion, such as tumor deformation, patient weight loss, or other patient changes. Assuming the projection time is 200 msec, the total latency, or the prediction length, is less than 300 msec, which is considered as short-term prediction. In addition, the MAO guided delivery is a negative feedback system that can self-correct prediction errors in later projections. Therefore, prediction accuracy is not in high demand and a simple linear prediction based on autoregressive modeling is found to work well in general for this application.

Let $x_i$ denote the tumor position of the i-th time sample. Linear prediction based on autoregressive modeling represents tumor motion as a linear combination of the past samples.

$$\alpha_1 x_{m+1} + \alpha_2 x_{m+2} + \ldots \alpha_n x_{m+n} = x_{m+n+k} \forall m \quad (33)$$

where n is the model order, k is the prediction length and $\alpha_i$'s are the coefficients to be calculated based on training data. We choose the model order n to correspond to approximately 2 sec motion data. The beginning 40 sec of the motion trace is used as training data and the coefficients are adaptively updated every 20 sec. According to our experiments on several real breathing curves, the accuracy of linear prediction can achieve about 0.5 mm in RMS errors for real respiration motion of peak-to-peak amplitude of 3 cm and latency of 300 ms.

We also need to predict PDF of tumor motion for future dose estimation, Eq. (21). But we simply use ~20 sec of past data to approximate PDF of future tumor motion. The accuracy of future dose estimation is again not very crucial due to the self-correcting feature of a closed-loop system.

2. Results

We used both simulated and clinical data to evaluate real-time MAO guided TomoTherapy$^{SM}$ treatment delivery. The same motion-encoded dose calculation engine as described in (Lu, 2008b) was used to calculate the delivered dose. All doses were calculated and DVHs were evaluated in the same reference frame as in the planning. We compared doses of the following three different delivery conditions.

1. SD: regular delivery with a stationary tumor
2. MD: regular delivery with a moving tumor
3. MAO: motion-adaptive-optimization guided delivery with the same tumor motion as in 2.

In addition, we also calculated dose of the MAD technique for comparison.

2.1 Simulated Data

For binary MLC based IMRT, such as TomoTherapy or TopoTherapy$^{SM}$ treatment delivery, the effects of intra-fraction motion are more pronounced in the longitudinal direction (Z-direction or the couch motion direction) than in the transverse direction. Our study first focused on longitudinal motion and then extended to 3D motion. For all simulations, we used the jaw width of 1.05 cm, gantry period of 10 sec, projection per rotation (PPR) of 51 and pitch of 0.3. These delivery parameters correspond to the worst case scenario for treatment delivery without motion compensation.

We used the 1D simulation as given in Lu, 2008a to study the effects of longitudinal motion. Because the motion was only longitudinal, the results applied to both static and helical delivery mode. We compared results of MAD, and MAO guided deliveries. Uniform dose distribution was intended for an 8 cm long target. The projection time was 196 msec (=10 sec per rotation/51 projections per rotation). The planned sinogram was a simple rectangle-shaped profile, corresponding to the leaf open time of 131 msec (=196 msec/MF) in the tumor region and zero elsewhere. Here, MF (=1.5) denotes the modulation factor used in the simulation.

FIGS. 8-14 illustrate the results. In all those figures, the top graph shows the longitudinal motion traces, the middle graph shows the planned and the delivery sinograms, and the bottom graph compares doses of SD, MD and MAD (FIG. 8, FIG. 10, and FIG. 12) or MAO (FIG. 9, FIG. 11, FIG. 13, FIG. 14).

Figure 8:
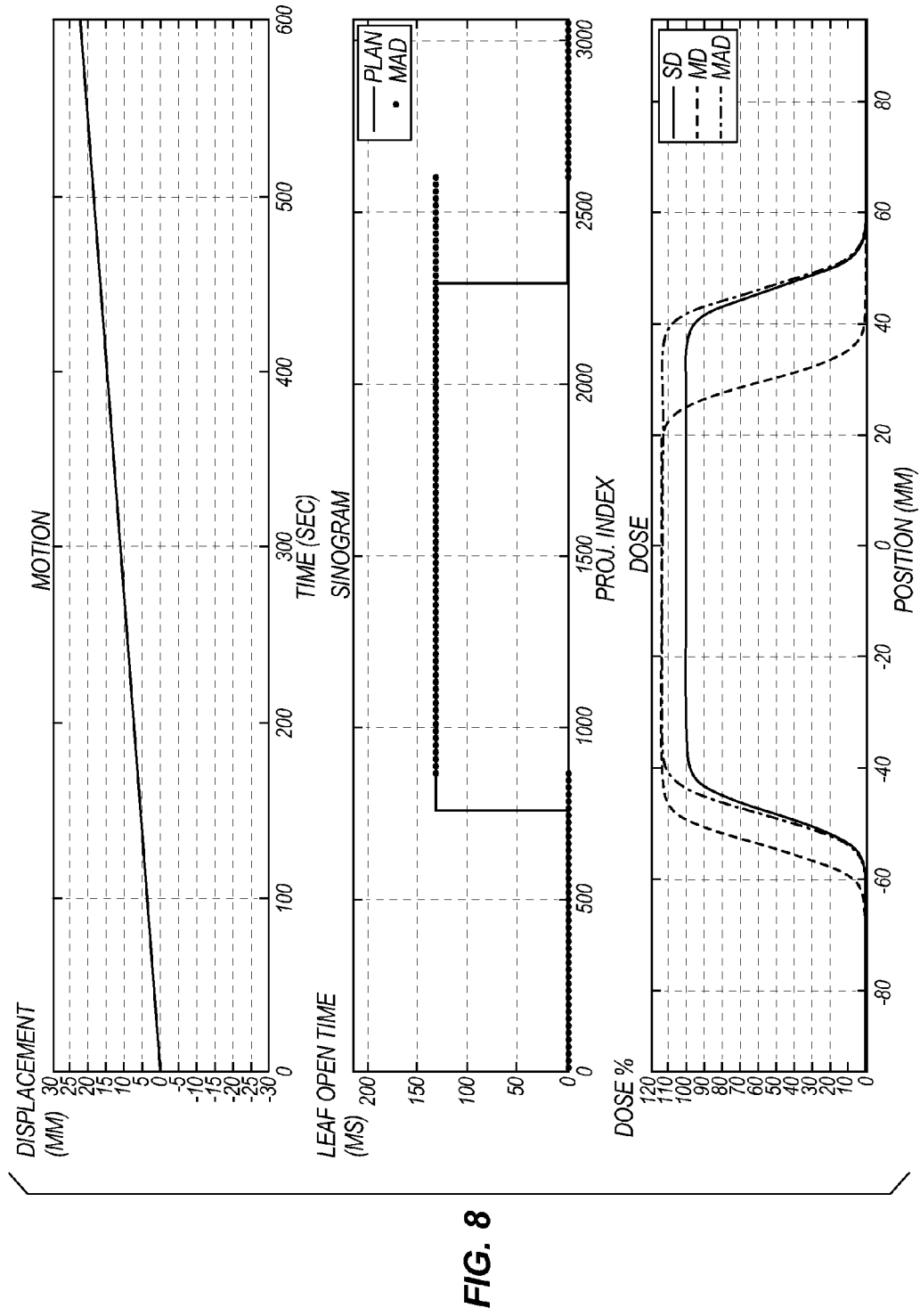
FIG. 8 graphically illustrates simulation results for real-time MAD delivery of a 1D rectangle-shaped dose profile.
Figure 9:
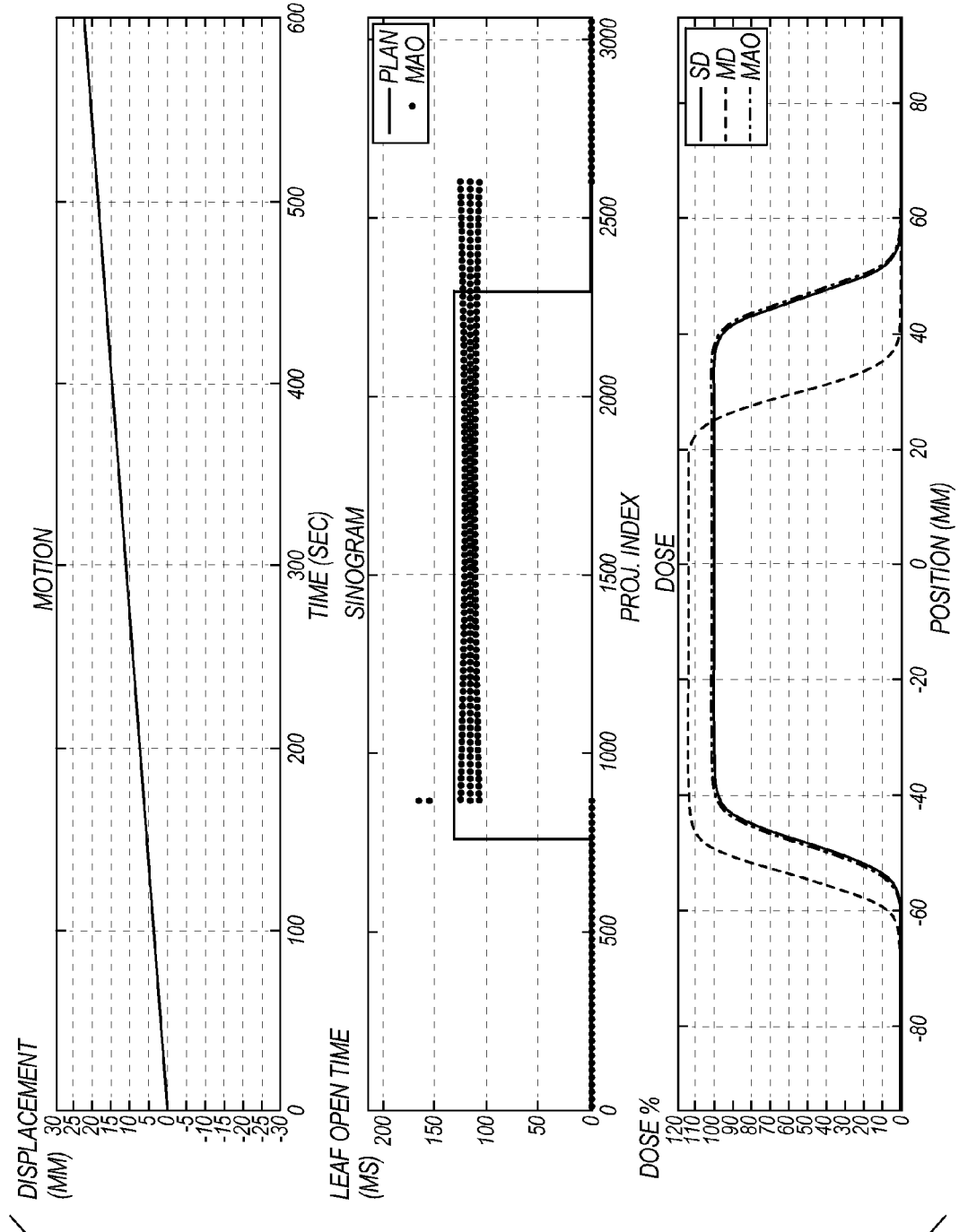
FIG. 9 graphically illustrates simulation results for real-time MAO guided delivery.

FIGS. 8-9 simulate motion of constant speed (~10% of the couch speed). This kind of motion arises when either the tumor moves downstream the radiation beam (against the couch moving direction) or the couch moves 10% slower than planned. Without compensation, such motion will result in 1) a part of the target missing and normal tissue overdosed because of the "dynamic" misalignment, and 2) a part of the target approximately 10% overdosed because it spends 10% more time than planned under the radiation beam. These effects are clearly illustrated by MD doses (the green dashed lines in the bottom graphs). The MAD dose aligns well with the planned dose (SD) with respect to the target boundary, but it is as "hot" as the MD dose in other regions. By rearranging the delivery sequence, MAD ensures radiation delivered to the right locations but it does not modify beam intensity to compensate for the downstream motion of the tumor. The MAD sinogram (shown as "dots" in the middle graph of FIG. 8) has the same intensity level as planned. If we knew the whole motion trace beforehand and did the global re-optimization for all projections, we would get the sinogram with intensity approximately 10% lower than planned in the tumor region. The MAO technique re-optimizes the beam intensity to compensate for the cumulative motion-induced error at every projection. FIG. 9 shows the result of MAO. As revealed in the middle graph of FIG. 9, the MAO sinogram oscillates at about 10% below the planned sinogram. The oscillation indicates the robustness of the negative feedback system of the MAO method. At each projection, the MAO algorithm compensates for the cumulative errors from all previous projection. Such compensation is by no means perfect due to the limitation of the delivery configuration (e.g., maximum leaf open time per projection) and the uncertainty of the prediction and future estimation. But both the compensation error and the prediction error can be further corrected by the coming projections. Through the negative feed back system, the MAO dose shown in the bottom graph of FIG. 9 perfectly matches the planned dose (SD).

Figure 10:
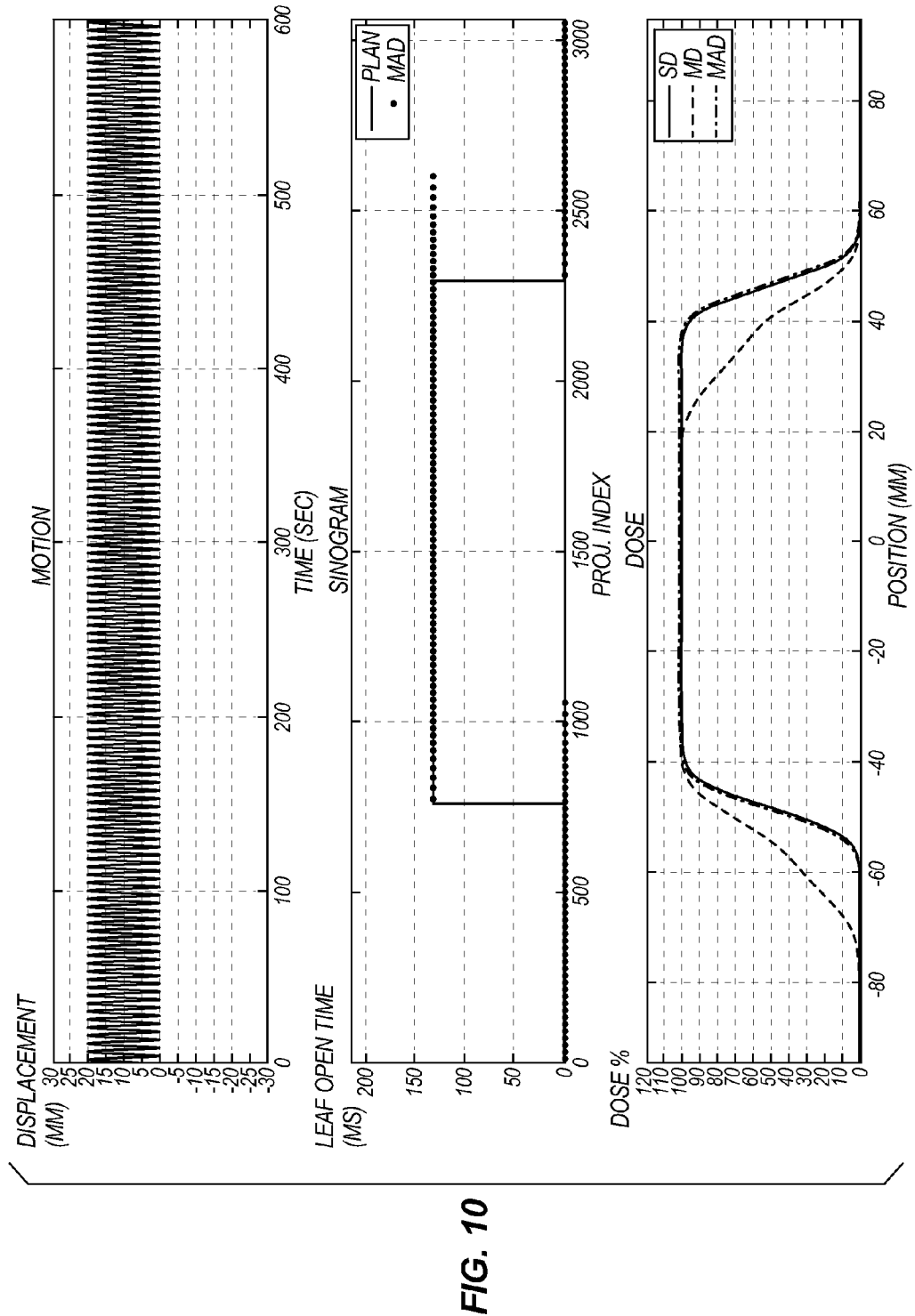
FIG. 10 graphically illustrates simulation results for real-time MAD delivery with the motion in the top graph simulating Lujan type regular respiration with T=4.3 sec, A=20 mm, b=0, and n=3.
Figure 11:
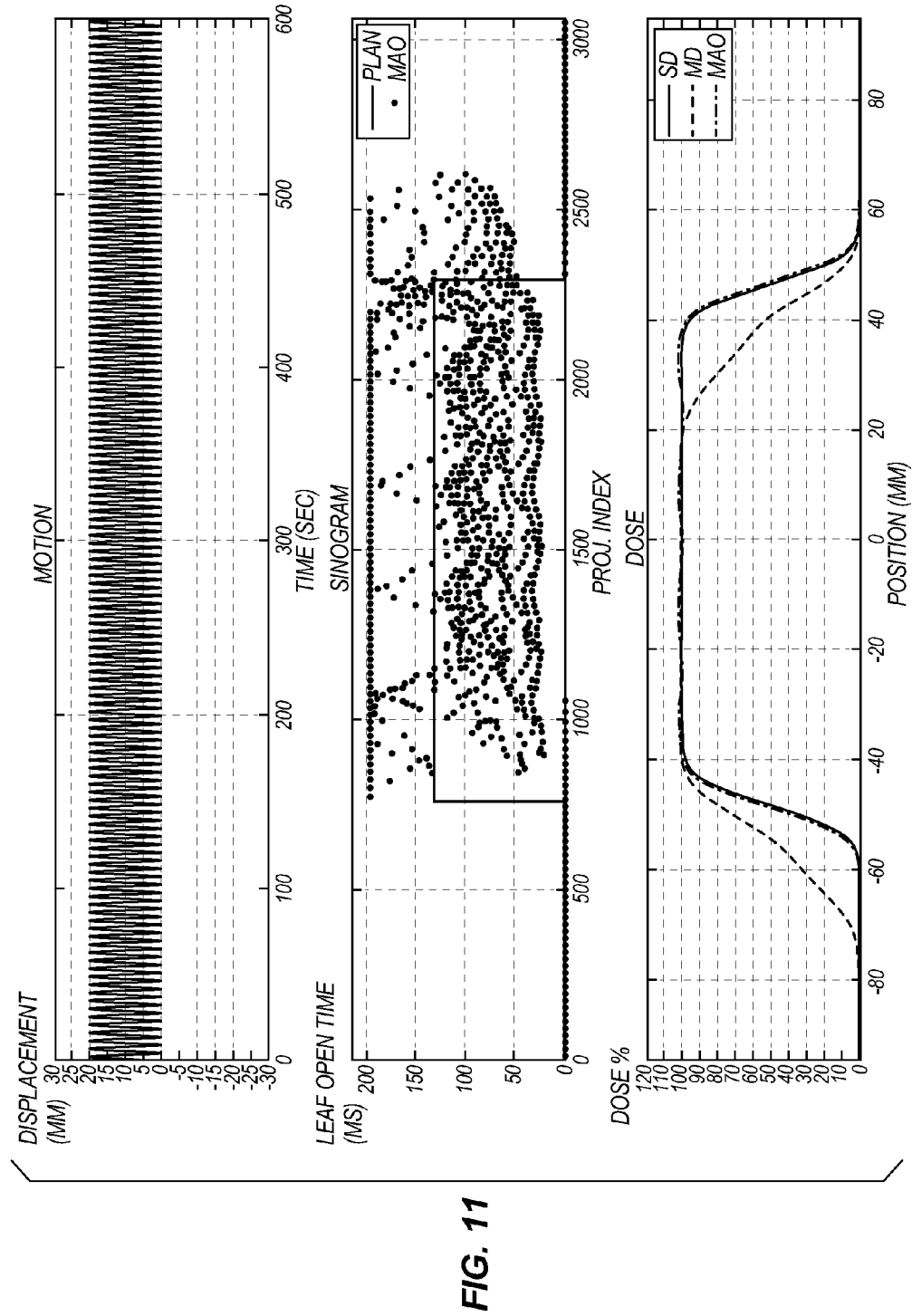
FIG. 11 graphically illustrates simulation results for real-time MAO guided delivery.

FIGS. 10-11 are for respiratory motion of the Lujan type with the peak-to-peak amplitude of 2 cm and period of 4.3 sec. As illustrated in the bottom graphs of both figures, the MD dose deviates significantly from the SD dose in both the front and back ends of the dose profile because of the respiratory motion. On the other hand, both the MAD and MAO methods compensate for the motion and their respective dose matches the SD dose very well. Although the MAD and MAO dose are almost identical, their sinograms are dramatically different (the middle graphs of FIGS. 10-11). The MAD sinogram has the same flat shape as planned, while the MAO sinogram shows great oscillation. Different sinograms may give almost identical doses, because the beamlet matrix consists of highly redundant beamlets. For PPR of 51 and the pitch of 0.3, each voxel will receive direct irradiation from 51/0.3=170 projections. Such redundancy implies existence of multiple solutions for a same objective and feasibility of compensation for cumulative errors using the greedy based optimization scheme of MAO.

Figure 12:
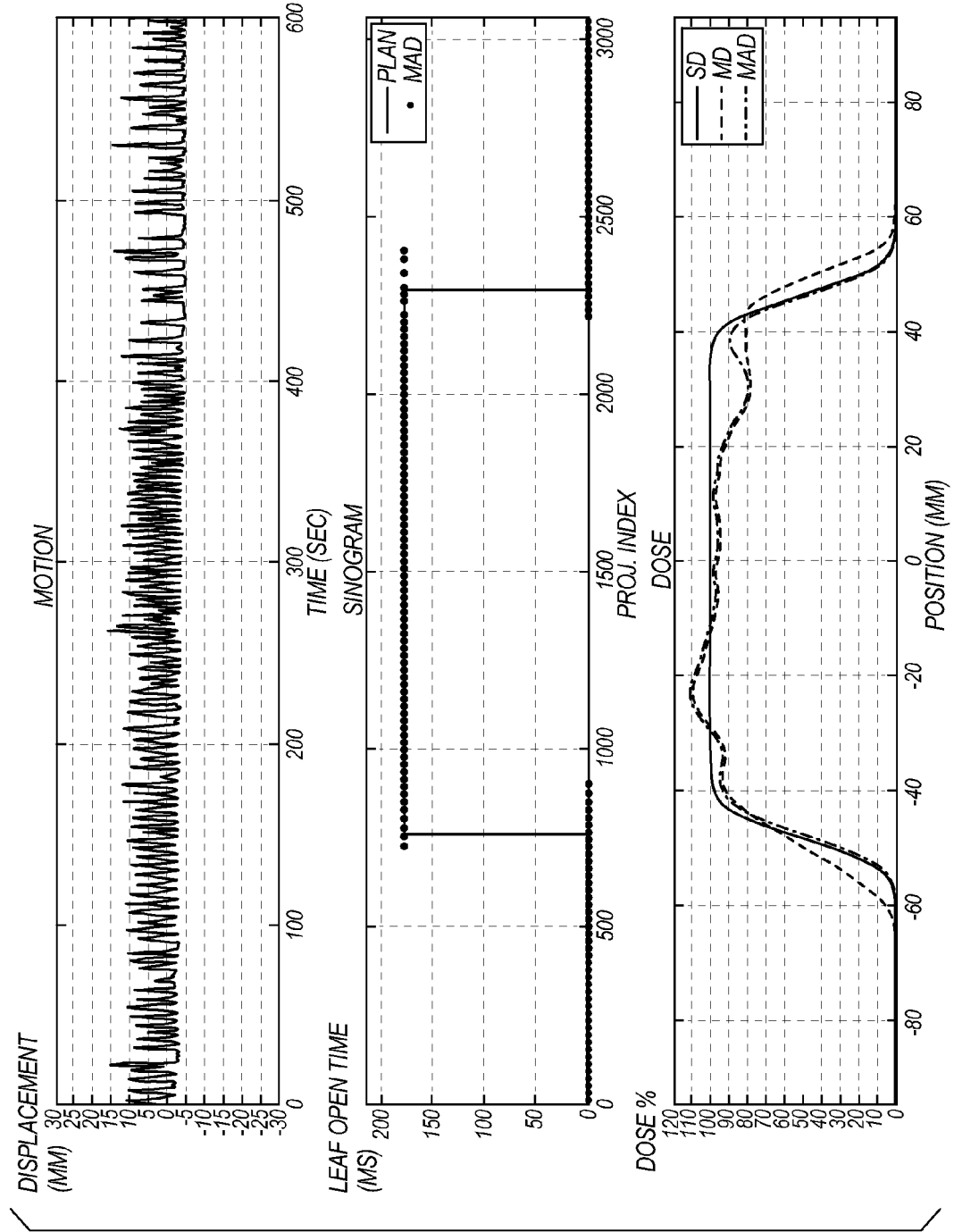
FIG. 12 graphically illustrates simulation results for a respiratory trace (top graph) measured from a real lung cancer patient.
Figure 13:
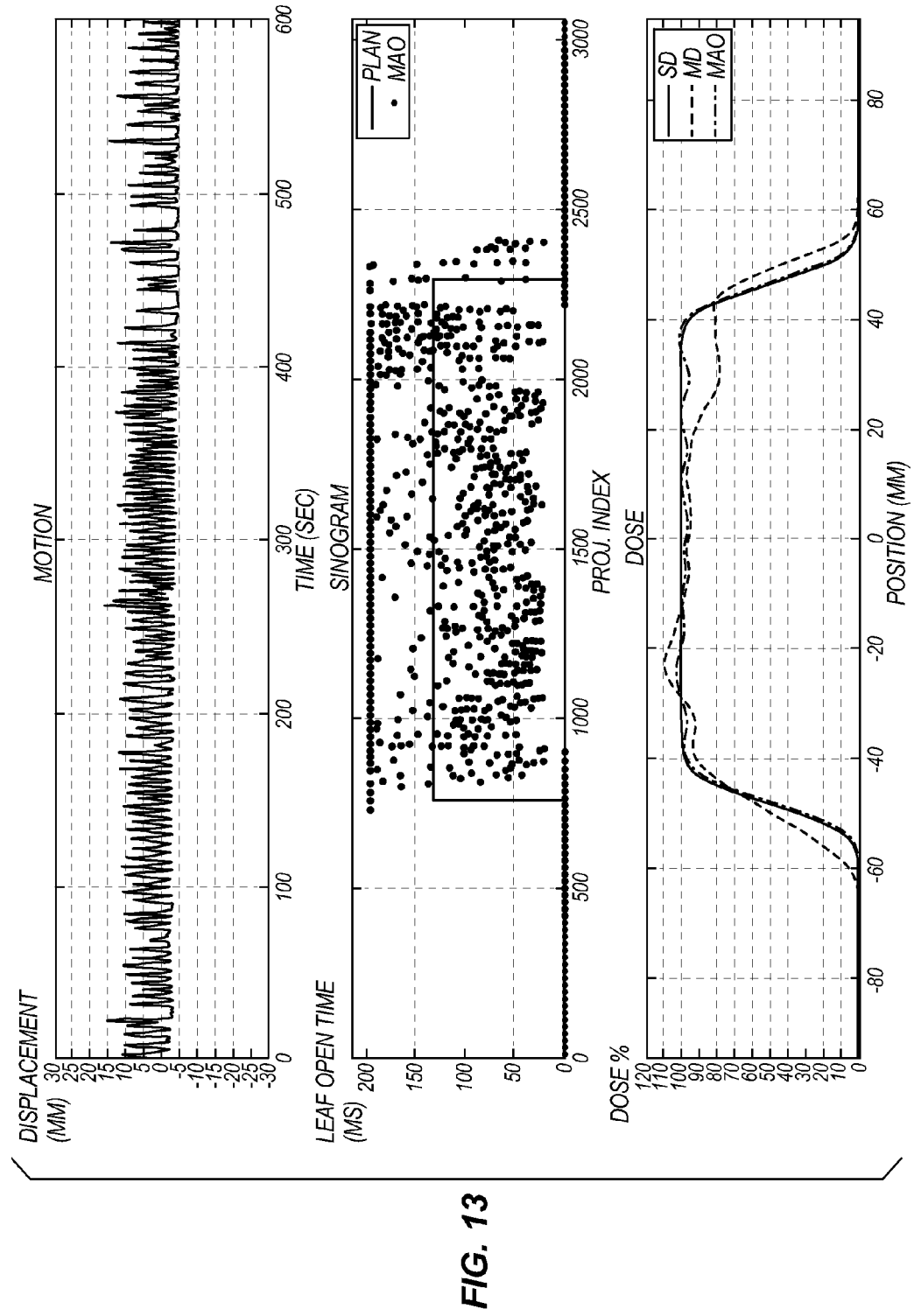
FIG. 13 graphically illustrates simulation results for a respiratory trace for real-time MAO guided delivery.
Figure 14:
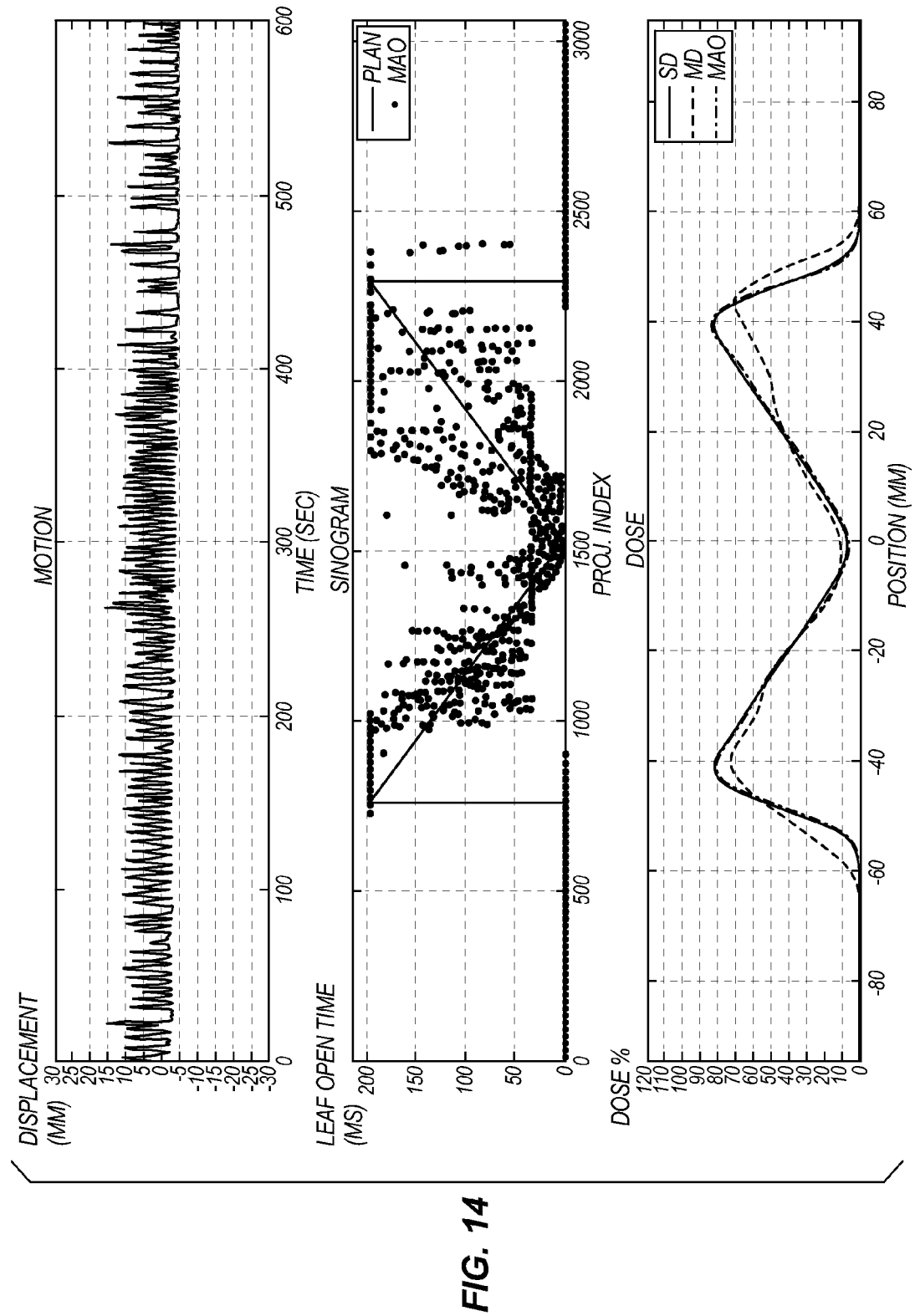
FIG. 14 graphically illustrates simulation results for an M-shaped plan sinogram.

FIGS. 12-13 show the results of an irregular respiration with the peak-to-peak amplitude of 2 cm measured from a lung cancer patient. The combination of the large amplitude of the very irregular respiration, small field size (1.05 cm) and fast gantry rotation (10 sec) of TomoTherapy$^{SM}$ treatment delivery results in high tumor dose non-uniformity in the MD dose shown in the bottom panels. The MAD dose again matches the SD dose well in the boundary of the tumor, but has the same non-uniformity as the MD dose in the inner region of the tumor (FIG. 12). On the other hand, the MAO method reduces edge blurring and tumor dose non-uniformity effects of irregular respiration to within 3% difference from the SD dose (FIG. 13). FIG. 14 shows the results of MAO for the same irregular respiration but with an M-shape intensity map, which simulates a highly intensity-modulated plan. It shows that the MAO dose matches the SD dose well even with such highly modulated plan.

MAD failed for the types of motion in FIGS. 8 and 12, because it is based on the assumption that each tumor voxel has the same chance to be irradiated as what was planned and both motion of constant velocity (FIG. 8) and very irregular respiration (FIG. 12) violate this assumption significantly. The real-time MAO method, however, is not based on such assumption, and thus suits well for arbitrary motion.

2.2 Clinical Data

The real-time MAO guided delivery technique can be applied to any kind of motion. Here we present the results of two kinds of motion: respiratory motion and prostate motion.

2.2.1 Respiratory Motion

We studied retrospectively a lung cancer case with the tumor size of approximately 2 cm in the inferior part of the lung. A treatment plan was optimized using TomoTherapy® Hi-Art® II TPS with the jaw width of 2.5 cm and pitch of 0.3. The optimization used the GTV (Gross Tumor Volume) as the target without any motion margin. The planned dose distribution is shown in the top row of FIG. 17. Because we did not have the respiration data for that patient, two different respiration traces of the spirometer signals from other lung cancer patients were used to simulate the tumor motion of the studied patient. The measured spirometer signals were 1D only and provided the relative amplitude and phase information. We scaled the signal amplitude so that the range of its lower 10% to upper 10% roughly corresponds to 3 cm in the SI direction, 2 cm in the AP direction and 1 cm in the LR direction. These motions are close to the maximum respiratory motion reported in the literature. For each motion trace, we calculated the MD and MAO dose and compared them with the SD dose. We also compared their DVHs.

Figure 15:
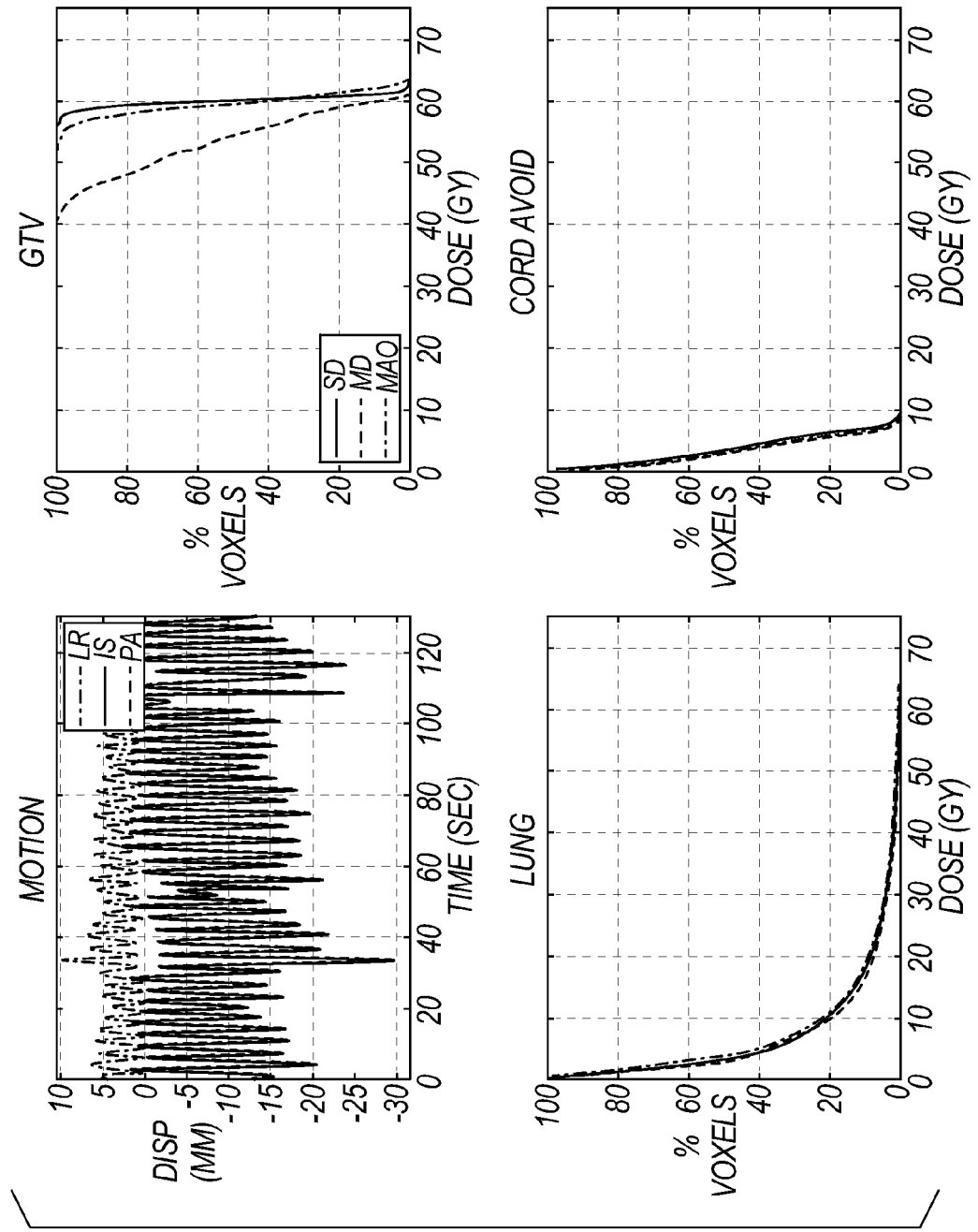
FIG. 15 illustrates DVH comparisons of different delivery methods for a lung cancer patient under TomoTherapy treatment.
Figure 16:
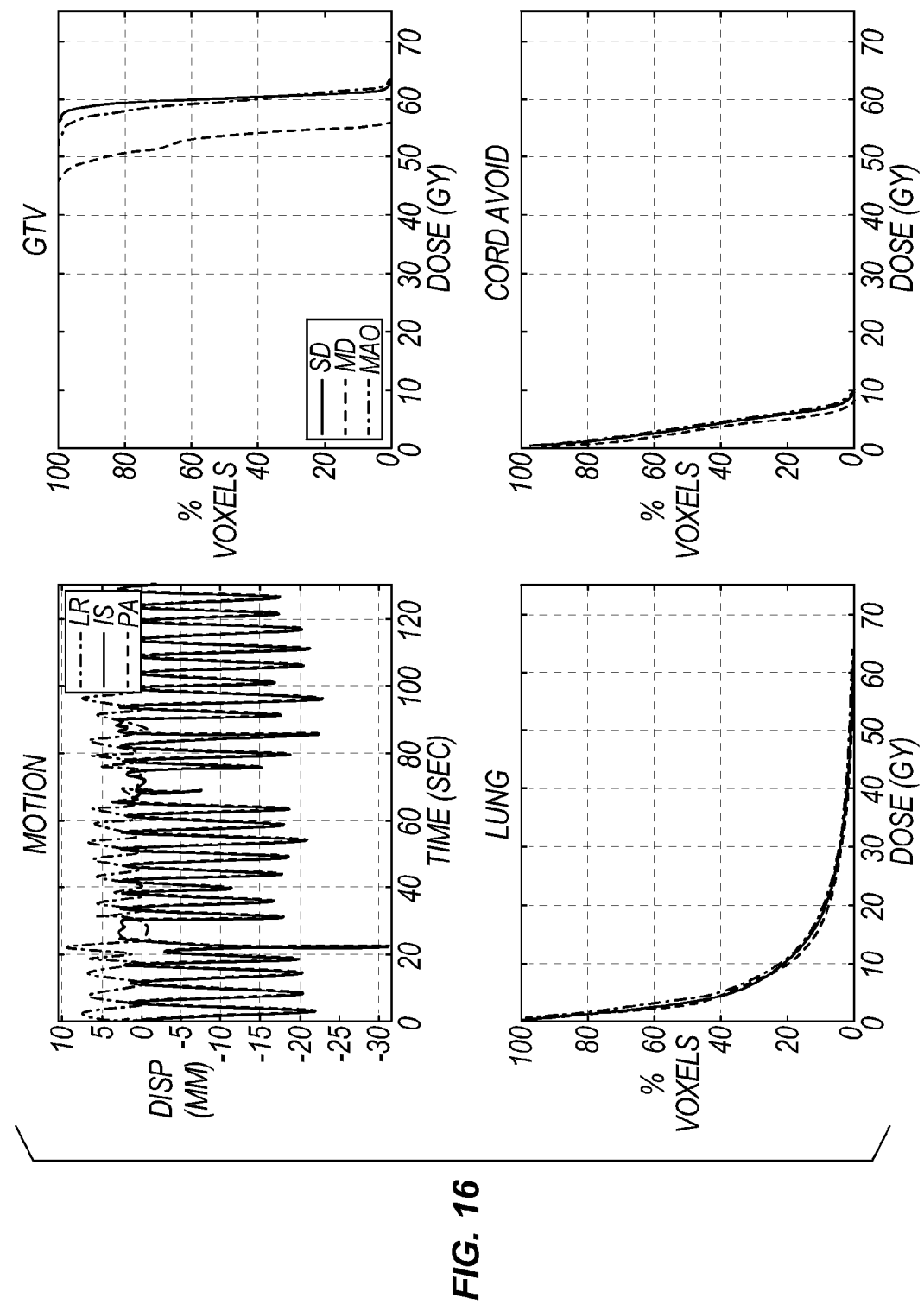
FIG. 16 illustrates DVH comparisons of different delivery methods for a lung cancer patient under TomoTherapy treatment for a different respiration trace.

The motion trace and DVH comparisons for different delivery modes are shown in FIGS. 15-16. Both figures show significant cold spots in the MD dose. Note that this is an extreme case because the GTV is only about 2 cm and the motion is as large as 3 cm. In addition, without motion margin in the treatment plan, it is expected that significant cold spots will show up because the tumor may move out of the radiation field. But even with no motion margin, the DVHs of MAO match the planned DVHs (SD) very well with negligible cold spots. These examples imply that the real-time MAO technique is an effective way to reduce the margin for treatment of a small lung tumor that undergoes significant respiratory motion.

Figure 17:
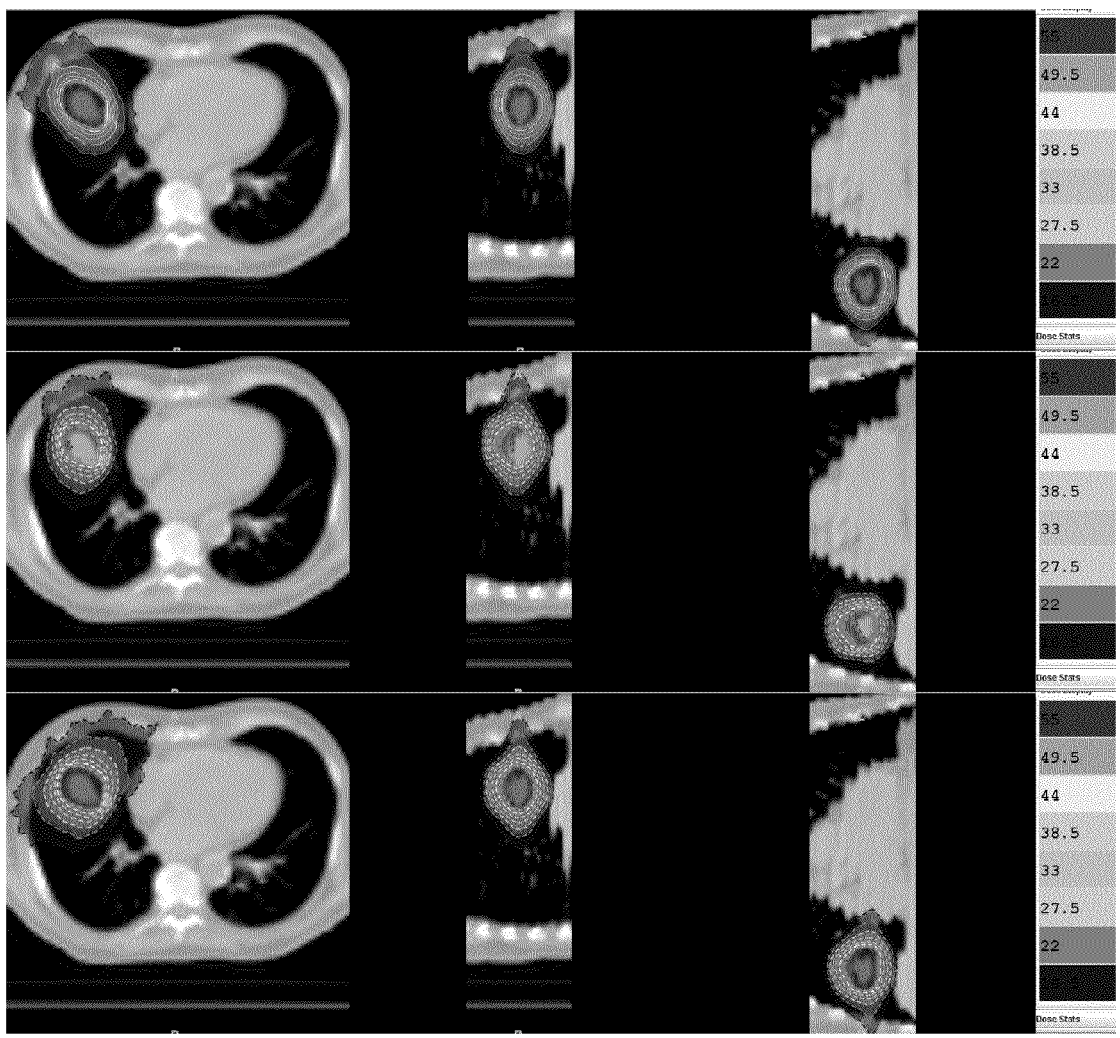
FIG. 17 illustrates dose distributions for the case shown in FIG. 16.

FIG. 17 compares the dose distribution in the transversal (T), sagittal (S) and coronal (C) views for the motion trace given in FIG. 16. The top row are the TSC views of the SD (planned) dose distribution, the middle row, of the MD dose distribution, and the bottom row, of the MAO dose distribution. It provides similar information as that of DVHs. Without motion compensation, the GTV dose is significantly less than the planned dose as shown in the isodose levels. With MAO guided delivery, the isodose lines in the high dose region (surrounding the tumor) are very similar to those of the SD dose, though there is some discrepancy in the low dose region. Such discrepancy is mainly due to scatter which is not fully modeled in MAO because of memory limitation. Also note that in all calculations, we assume a rigid-body motion, which is quite valid for a small tumor, but not for the lung or the spinal cord. Therefore, the results of the lung and the spinal cord dose should be read with caution, though we would expect that the difference is minimal when the tumor is small and far away from the spinal cord.

2.2.2 Prostate Motion

We studied retrospectively the same prostate patient cases as reported in (Langen et al., 2008b, Langen et al., 2008a). The intra-fraction prostate motions were real-time tracked via the electromagnetic signals of a four-dimensional localization system of Calypso®. These motions were classified into small, medium or large prostate displacements, which correspond to amplitudes of less than 3 mm, between 3 to 5 mm or larger than 5 mm and account for more than 85%, ~10% or ~3% of all tracking data, respectively, as described in (Langen et al., 2008c). The same optimized treatment plans as in (Langen et al., 2008b, Langen et al., 2008a) with the jaw width of 2.47, pitch of 0.287 and gantry rotation period of 29 to 31 sec. were used.

Figure 18:
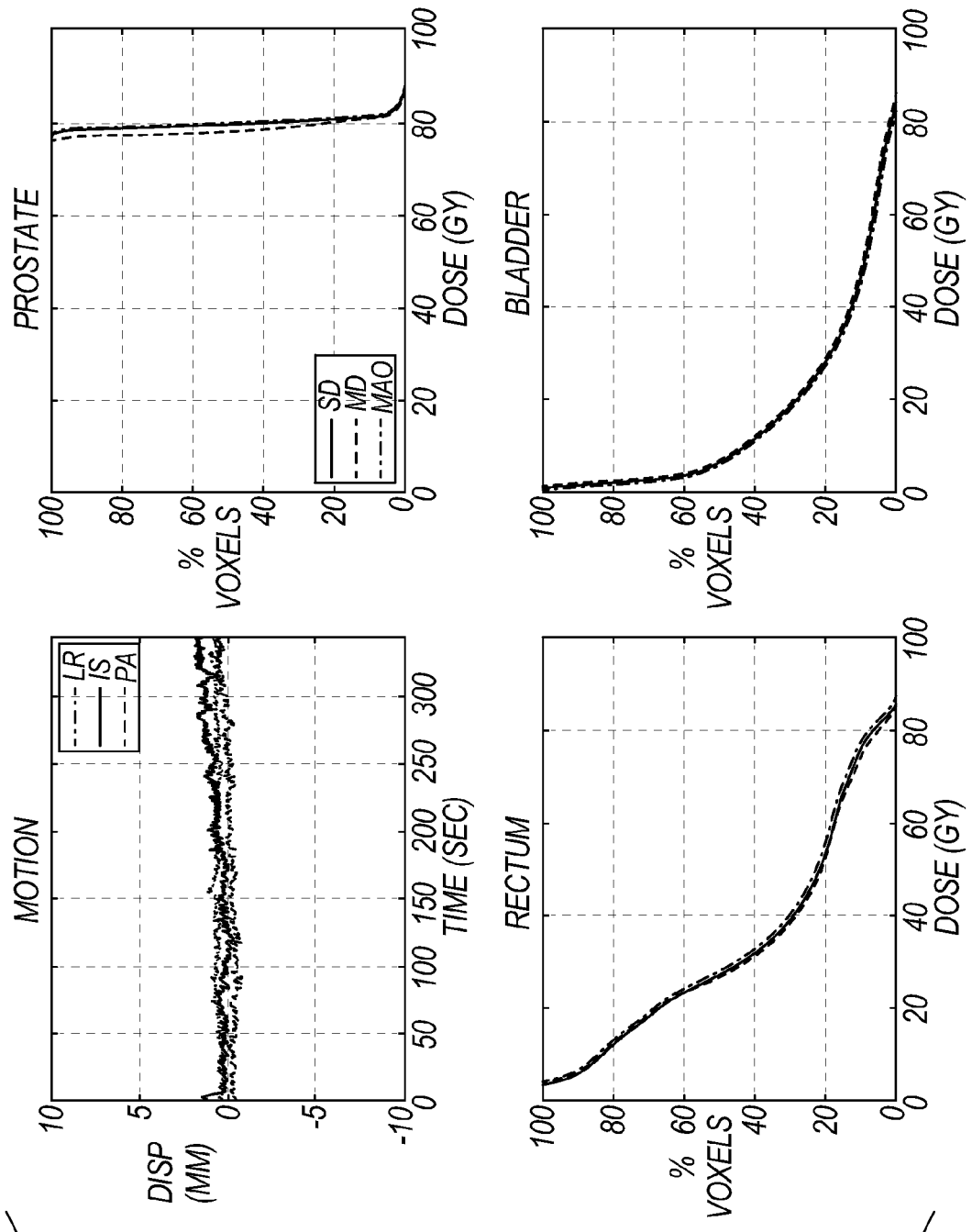
FIG. 18 illustrates DVH comparisons of different delivery methods for a prostate cancer patient under TomoTherapy treatment.

FIG. 18 shows the results of a small prostate motion that is within 3 mm during the whole treatment. DVHs of MD are slightly below those of SD, and DVHs of MAO perfectly match those of SD, which indicates the robustness of the MAO method for such small motion.

Figure 19:
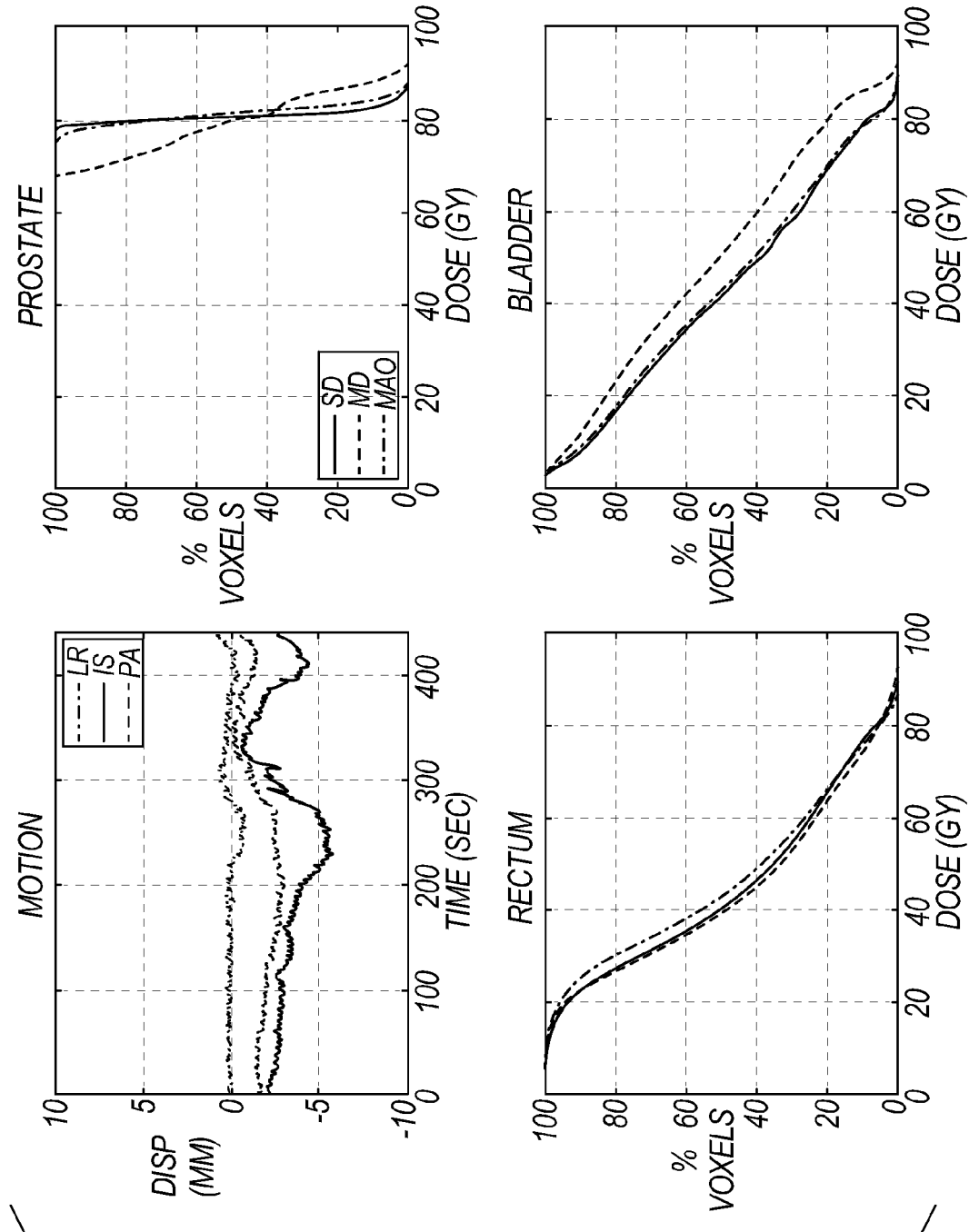
FIG. 19 illustrates DVH comparisons of different delivery methods for a prostate patient undergoing intra-fraction prostate motion.

FIG. 19 shows the results of a medium prostate motion. The prostate moved between 3 mm and 6 mm in the SI (superior-inferior) direction for a significant amount of time. Both hot and cold spots appeared in the prostate DVH of MD compared with that of SD. This is because, in the SI direction, the tumor moved both upstream (against the radiation source motion) and downstream (following the radiation source motion), as indicated by the SI motion trace in the top left panel. The upstream motion caused parts of the prostate receiving lower-than-planned dose, while the downstream motion caused other parts higher-than-planned dose. The MAO technique was able to compensate for both motions as illustrated in the DVH plots. The prostate DVH of MAO approached that of SD well. In addition, the hot spots in the bladder were corrected by MAO.

Figure 20:
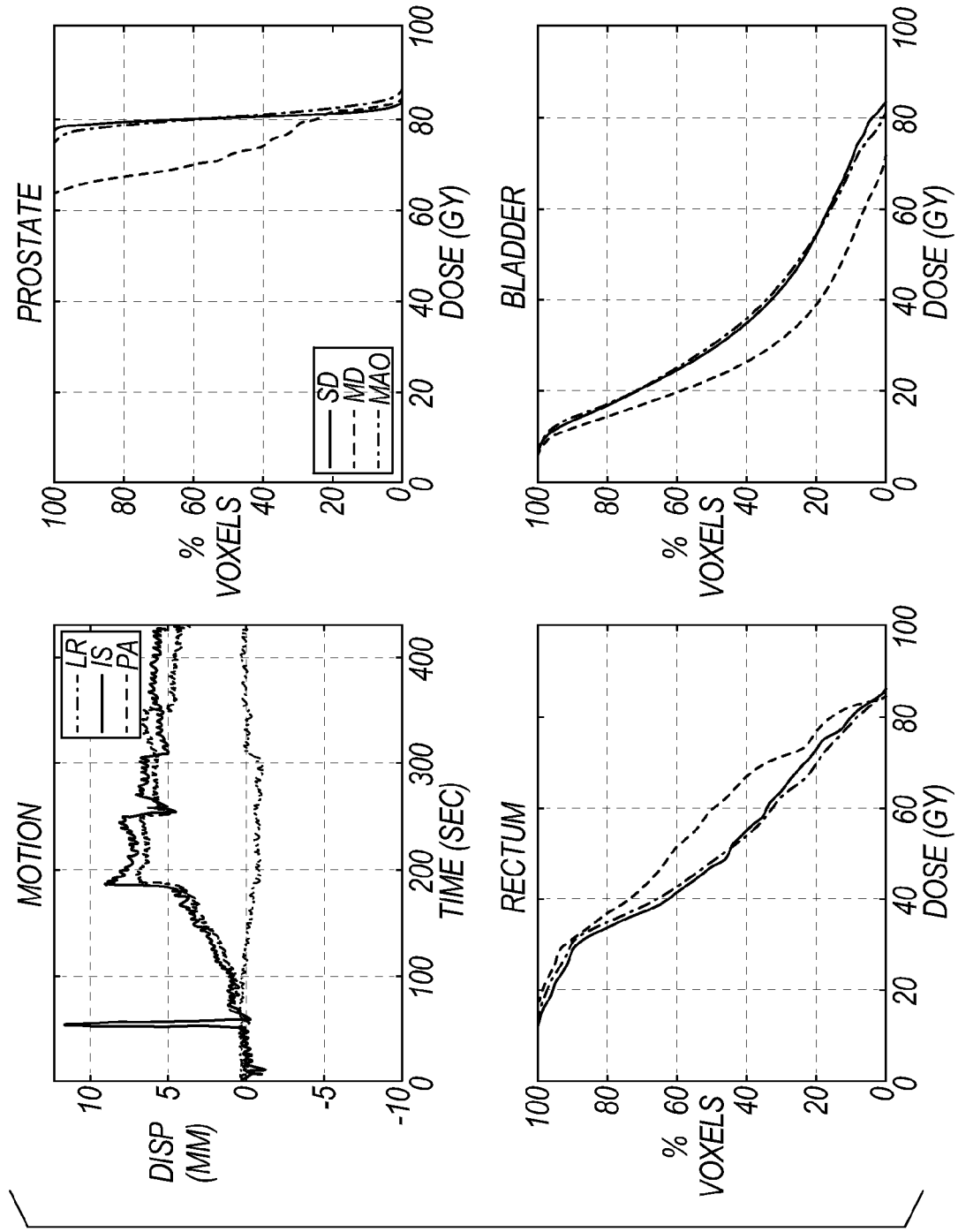
FIG. 20 illustrates DVH comparisons of different delivery methods for a prostate patient undergoing intra-fraction prostate motion.
Figure 21:
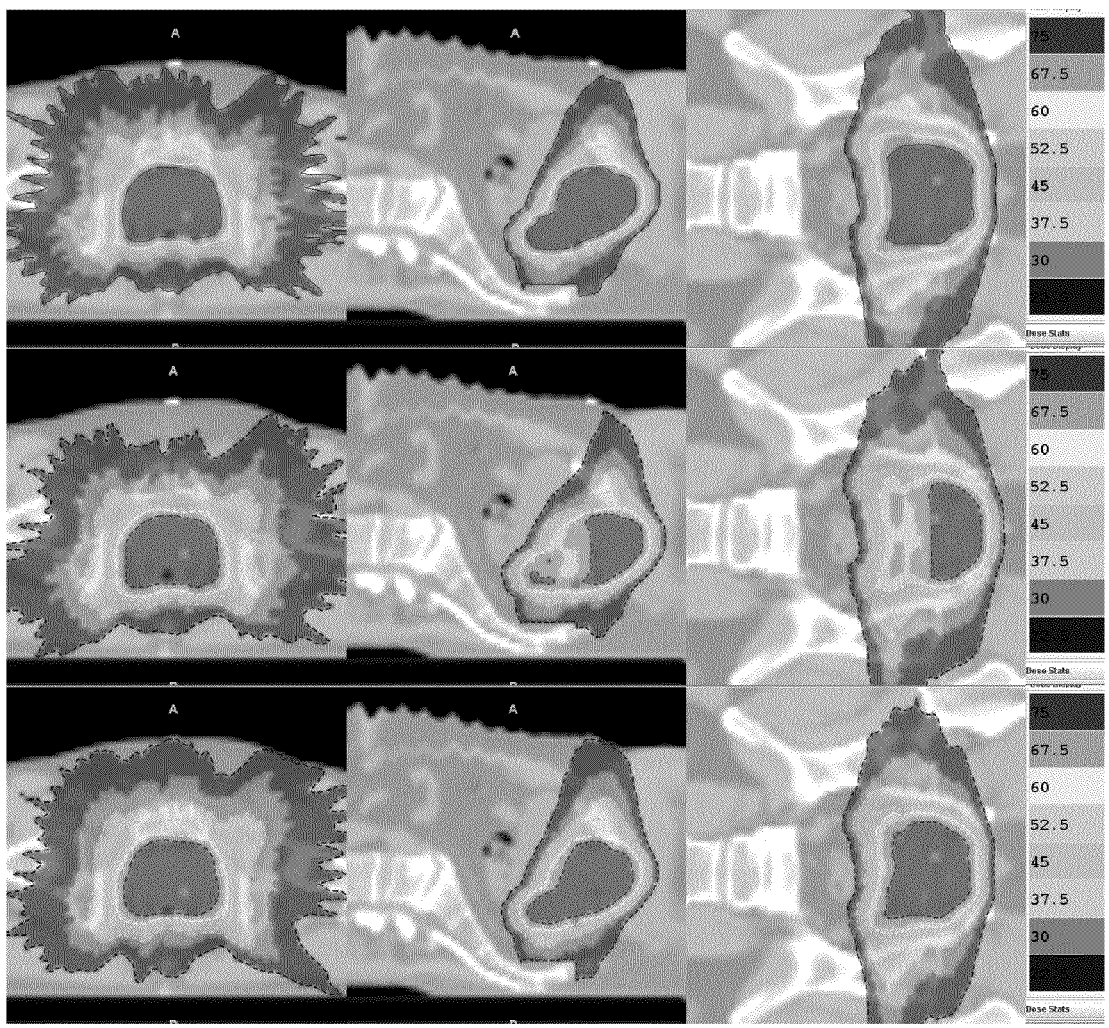
FIG. 21 illustrates dose distributions for the case shown in FIG. 20.

FIGS. 20-21 show the results for a large prostate motion. The top row of FIG. 21 shows the planned (SD) dose distribution in TSC views, the middle row, the MD dose distribution, and the bottom row, the MAO dose distribution. The prostate moved between 5 mm and 10 mm in both the SI and AP (anterior-posterior) directions for most delivery time. Such large upstream SI motion caused significant cold spots in the prostate dose distribution, detected by the prostate DVH (FIG. 20) and dose distribution of MD (the middle row of FIG. 21). On the other hand, the MAO technique compensated for such large motion quite well. The MAO isodose lines (the bottom row of FIG. 21) were very similar to the planned dose (the top row of FIG. 21) and the DVHs of MAO approached those of SD (FIG. 20). Note that the hot spots in the rectum were corrected by MAO.

These examples show that real-time MAO can effectively compensate for prostate motions of all kinds, small or large, though, such motion effects are usually quite mild and quickly washed out after five fractions of delivery. Here we assumed rigid body motion for all studies. Such assumption is arguable for the prostate and definitely not suitable for the bladder and the rectum. Therefore, both the MD and MAO results presented here should be read only as proof of concept rather than clinical guidance.

3. Discussion

Figure 22:
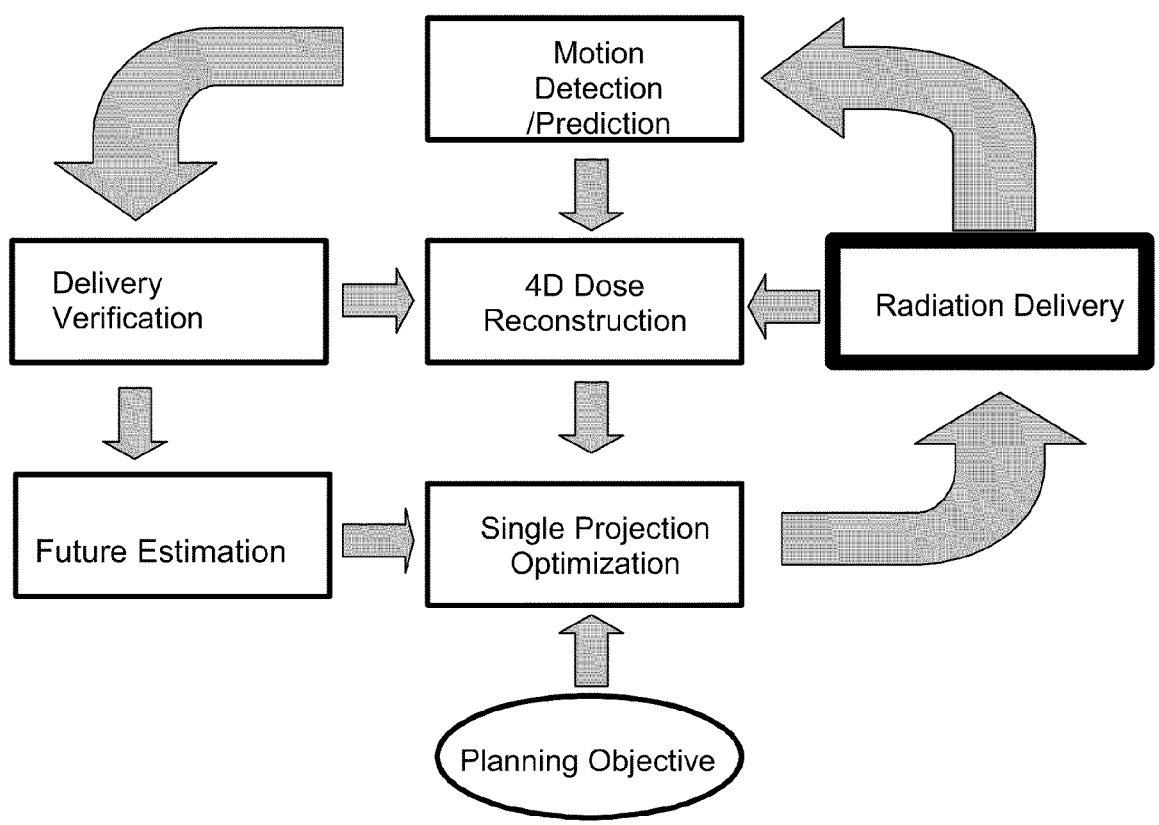
FIG. 22 is a flow chart illustrating real-time ART.

Treatment planning is based on information about the commissioning data of the delivery machine and the patient anatomy such as CT. Because the goal of treatment delivery is to reproduce the treatment plan as accurately as possible, the delivery procedure should be accurately modeled in treatment planning. However, real-time changes, such as tumor motion, are hard to be accurately modeled in advance. The state-of-the-art radiation delivery is an open-loop procedure. It tries to reproduce the planned procedures step-by-step, but lacks the mechanism to deal with the error occurred and accumulated in each step. The proposed real-time MAO guided radiotherapy changes the delivery scheme from a conventional open-loop system to a closed-loop system with negative feedback. In this sense, the framework of MAO can be easily extended to a more general scheme, real-time adaptive radiation therapy (ART), as illustrated in FIG. 22. In this flow chart, both motion errors (derived from patient motion and other patient changes) and machine errors (derived from various machine parameters) are detected and predicted in real-time. A 4D dose reconstruction engine accumulates the delivered dose in real-time. The reconstructed dose, together with future estimation, is used to drive the real-time optimizer that optimizes the leaf open time for the coming projection.

ART generally refers to the concepts of using feedback during the course of radiation therapy to improve future treatment. Feedback can be used for off-line adaptive processes or on-line processes. Off-line ART refers to processes when the patient is not being treated, such as in between treatment fractions, whereas on-line ART refers to processes when the patient is on the treatment couch but right before delivery of the treatment beam. Both off-line and on-line ART are to compensate for the inter-fractional changes. Real-time ART, however, is to correct intra-fractional, or real-time, generated errors, whether they are due to patient motion or random machine variations, such as linac output changes, leaf open errors, gantry rotation errors, couch motion errors, etc. The instructions for driving radiation delivery in real-time ART are optimized in real-time with systematic feedback from many components, including machine parameters and patient changes (such as changes due to patient motion). Real-time ART imposes high demand on error detection and system response. Real-time dose reconstruction will also be a critical component for real-time ART. The real-time optimization workflow should be able to accomplish real-time ART for TomoTherapy$^{SM}$ treatment delivery, provided we establish reliable implementation of motion detection, delivery verification and dose reconstruction.

Intra-fractional motion, such as respiratory motion, heart beat and other physiological changes, is challenging for conventional fractionated IMRT. The more dynamic the treatment modality, the more important the identification of intra-fraction changes, both due to motion and machine parameter changes or errors, becomes.

But it is even more challenging for stereotactic body radiation treatment (SBRT) and hypofractionated therapy, where precise target positioning is critical. SBRT is increasingly being used in certain lung cancers because of its rate of local control. Hypofractionation for prostate cancer has the potential of therapeutic gain as well as economic advantage. Both lung and prostate cases demonstrate significant intra-fractional motions. Intensity Modulated Proton (or other heavy particles) Therapy requires most critical motion management. The proposed real-time MAO technique can potentially be applied in all those three therapy modes.

The proposed MAO technique still falls in the category of "compensation" that regards motion as "error" to be corrected. Motion is a challenge, yet motion is also a chance. Just as we can take advantage of inter-fractional variations of the tumor-OAR configuration to achieve better therapeutic gain through "Adaptive Fractionation Therapy," we can potentially also take advantage of intra-fractional motion to achieve a "better-than-planned" delivery. This possibility was demonstrated by Papiez's group (Papiez et al., 2007) using 4D DMLC delivery to minimize the OAR dose. We believe that a more advanced real-time optimization scheme should be able to offer a superior delivery, which is not achievable via any plan based on static delivery. Such scheme may require more sophisticated algorithms and a powerful computer.

In this document, we assumed that tumor motion could be regarded as a rigid body shift and objects-at-risk ("OAR") move in the same way as the tumor. This is a good approximation for a small tumor and for an OAR that is close to the tumor. Motion compensation is more significant for small tumors than for large tumors and OAR close to the tumor is usually of more concern than those far away from the tumor. Therefore, we regard such assumptions as valid for the majority of tumor motion cases. The proposed real-time optimization scheme does not exclude rotation or general deformation. However, it requires a different formula from what was presented above to calculate deformation-encoded beamlets. The problem is then how to delineate faithfully the deformation in real-time. This may involve an ultra-fast deformable registration algorithm, or using pre-calculated deformation maps that are based on some 4D images such as 4DCT.

By utilizing the closed feedback loop, the method according to the present invention also allows for the prediction of machine parameters and patient changes. In one embodiment, the prediction can be based upon extrapolating information from the machine parameter and patient change/motion data gathered real-time. For example, predictions in machine parameters or patient motion can be based on identified machine trends or patient motion patterns. The method also contemplates teal-time optimization of the current delivery instructions, incorporating the information of the original treatment objective, cumulative dose received to date, and future dose delivery estimations.

Figure 23:
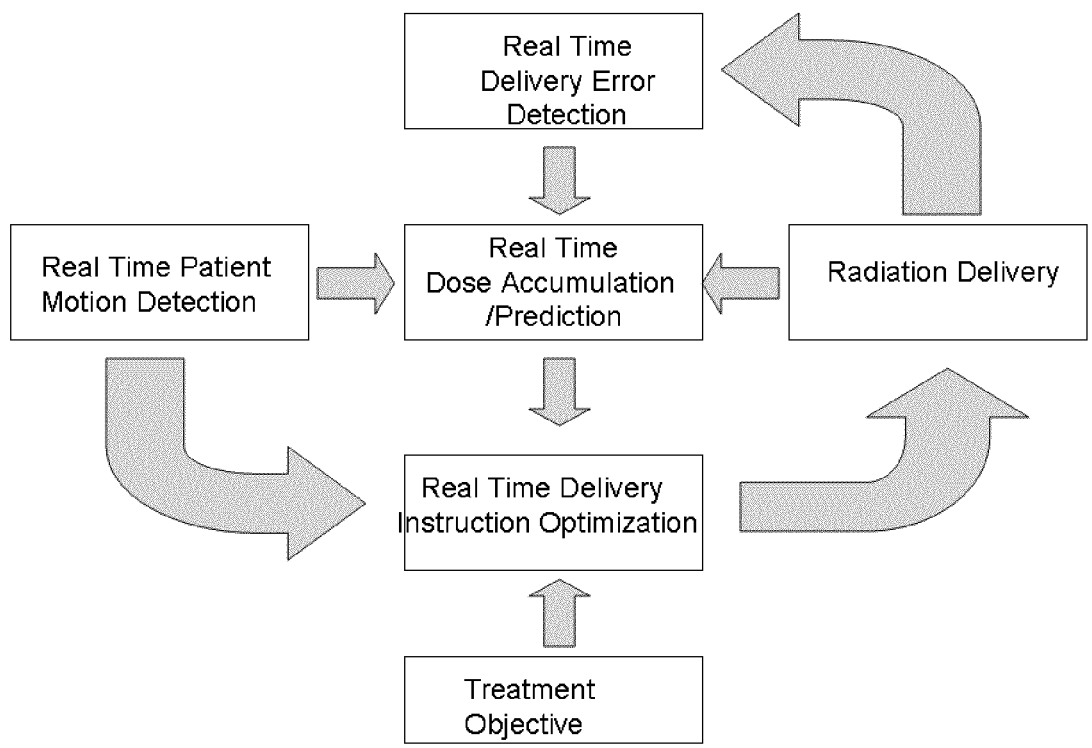
FIG. 23 is a flow chart illustrating a dynamic programming loop operable to optimize a treatment plan according to the invention.

One way to implement the closed feedback loop is using dynamic programming, as illustrated in FIG. 23. Dynamic programming optimizes the treatment delivery instructions in real-time and is utilized to ensure that the delivery instruction optimization keeps up with the real-time beam delivery to the patient. In one embodiment of the invention, each optimization loop utilizing dynamic programming begins with the step of collecting real-time machine parameter and patient motion information. In some embodiments, machine parameter and patient motion/change information is predicted for future treatment projections based on the real-time information collected. The dose from the most recent treatment projection is calculated, incorporating the information regarding machine parameters and patient motion.

In the next step, the most recent dose is added to the delivered dose to monitor the cumulative dose with respect to the expected dose delivered. The dose for the most recent delivered treatment projection is reconstructed in real-time with the machine parameter and patient motion information incorporated so that this dose can be added to the delivered dose in the reference framework. In some embodiments, it is not the delivered dose values themselves that are cumulated, rather the differences between expected and delivered doses are accumulated. From the cumulative dose information, estimations for future doses can be obtained using a model about patient motion and machine parameters. This model may be an a priori model, or may be a dynamic model.

The delivery instruction for the current plan is then optimized so that the combination of the current dose, plus previous dose delivered plus future dose best matches or improves the treatment objectives (i.e., the intended dose). The optimization includes generating an initial guess of the delivery instruction by choosing from a pool of delivery instructions that best matches the current machine parameters and delivery states, such that the addition of doses best matches the planning objective for the treatment. The dose information utilized can be representative point dose, a 1D dose profile, a 2D plane dose, a 3D dose distribution for the region of interest or whole body, or other quantities derived from dose distribution (such as dose volume histogram, equivalent uniform dose, biological effective dose, etc.).

The overall delivery error could be further compensated in subsequent real-time optimized fraction delivery. The overall delivery error, which is defined as the difference between the planning objective and the overall delivered dose, is added to the original planning objective to get a new planning objective for the following treatments with real-time optimization guided delivery.

While the previously-described method contemplates optimizing delivery instructions for a single projection, it is possible to apply this method to optimize delivery instructions for several treatment projections at the same time.

Various features and advantages of the invention are set forth in the following claims.

What is claimed is:

1. A method of delivering a radiation therapy treatment, the method comprising:
    generating a treatment plan for a patient, the treatment plan including a plurality of projections;
    positioning the patient to receive radiation from a radiation source based on the treatment plan;
    monitoring machine parameters during delivery of at least a portion of the plurality of projections in substantially real-time, the monitoring including analyzing information regarding the machine parameters and how the parameters affect dose delivered to the patient;
    during delivery of at least a portion of the plurality of projections, calculating an accumulated radiation dose delivered to the patient in substantially real-time;
    during delivery of at least a portion of the plurality of projections, optimizing at least a portion of the plurality of projections yet to be delivered to the patient in substantially real-time to incorporate the analyzed information from the monitored machine parameters and the accumulated radiation dose; and
    delivering at least a portion of the plurality of projections yet to be delivered to the patient as optimized.

2. The method of delivering a radiation therapy treatment of claim 1 wherein accumulating the amount of radiation dose delivered to the patient includes using dose calculations on a 4D representation of the patient.

3. The method of delivering a radiation therapy treatment of claim 1 further comprising estimating an amount of radiation dose to be delivered to the patient in a future projection.

4. The method of delivering a radiation therapy treatment of claim 3 further comprising adjusting the treatment plan based on the estimated amount of radiation dose to be delivered to the patient in the future projection and the predicted position of a patient target during the future projection.

5. The method of delivering a radiation therapy treatment of claim 1, wherein calculating the accumulated radiation dose incorporates information relating to at least one of delivery instructions, delivery error detection and patient motion detection.

6. The method of delivering a radiation therapy treatment of claim 1, wherein calculating the accumulated radiation dose includes accumulating current dose plus previous dose delivered plus future dose to be delivered so that the optimized plurality of projections best matches or improves the planned dose.

7. The method of delivering a radiation therapy treatment of claim 1, wherein calculating the accumulated radiation dose incorporates real-time modification of treatments.

8. The method of delivering a radiation therapy treatment of claim 1, wherein optimizing at least a portion of the plurality of projections yet to be delivered to the patient includes optimizing an amount of radiation dose to be delivered in one of the plurality of projections to compensate for accumulated delivery errors that occurred in previous projections.

9. The method of delivering a radiation therapy treatment of claim 8 wherein the accumulated delivery errors are based on the calculated accumulated radiation dose, an estimated radiation dose to be delivered in future projections, and a predicted configuration of the patient during a next projection.

10. The method of delivering a radiation therapy treatment of claim 8 wherein the accumulated delivery errors include delivery errors from previous fractions.

11. The method of delivering a radiation therapy treatment of claim 8, wherein the accumulated delivery errors include linear accelerator output factor variations.

12. The method of delivering a radiation therapy treatment of claim 8, wherein the accumulated delivery errors include MLC leaf position errors.

13. The method of delivering a radiation therapy treatment of claim 8, wherein the accumulated delivery errors include one of linac position errors, couch position errors, jaw position errors, and compensator errors.

14. The method of delivering a radiation therapy treatment of claim 8, wherein the accumulated delivery errors are compensated in subsequent treatment delivery.

15. The method of delivering a radiation therapy treatment of claim 1 wherein optimizing at least a portion of the plurality of projections yet to be delivered to the patient incorporates changes to the treatment plan via a closed feedback loop.

16. The method of delivering a radiation therapy treatment of claim 1 further comprising monitoring changes to the patient in substantially real-time.

17. The method of delivering a radiation therapy treatment of claim 16, wherein monitoring changes to the patient in substantially real-time includes detection of patient breathing phases.

18. The method of delivering a radiation therapy treatment of claim 16, wherein monitoring changes to the patient in substantially real-time includes detection of tumor motion or tumor deformation.

19. The method of delivering a radiation therapy treatment of claim 16, wherein monitoring changes to the patient in substantially real-time includes prediction of patient breathing phases.

20. The method of delivering a radiation therapy treatment of claim 16, wherein monitoring changes to the patient in substantially real-time includes prediction of tumor motion or tumor deformation.

21. The method of delivering a radiation therapy treatment of claim 16, wherein optimizing at least a portion of the plurality of projections yet to be delivered to the patient in substantially real-time comprises predicting patient changes.

22. The method of delivering a radiation therapy treatment of claim 1, wherein optimizing at least a portion of the plurality of projections yet to be delivered to the patient in substantially real-time comprises predicting machine parameters.

23. The method of delivering a radiation therapy treatment of claim 22, wherein the prediction is based upon an a priori model about machine parameters.

24. The method of delivering a radiation therapy treatment of claim 22, wherein the prediction is based on a dynamic model about machine parameters.

25. The method of delivering a radiation therapy treatment of claim 1, wherein optimizing at least a portion of the plurality of projections yet to be delivered to the patient in substantially real-time includes utilizing dynamic programming for optimization of treatment delivery instructions.

26. A method of delivering a radiation therapy treatment, the method comprising:
   generating a treatment plan for a patient, the treatment plan including a plurality of projections;
   positioning the patient to receive radiation from a radiation source based on the treatment plan;
   monitoring machine parameters during delivery of at least a portion of the plurality of projections in substantially real-time, the monitoring including analyzing information regarding the machine parameters and how the parameters affect dose delivered to the patient;
   monitoring changes to the patient during delivery of at least a portion of the plurality of projections in substantially real-time, the monitoring including analyzing information regarding the patient changes and how the changes affect dose delivered to the patient;
   during delivery of at least a portion of the plurality of projections, calculating an accumulated radiation dose delivered to the patient in substantially real-time;
   during delivery of at least a portion of the plurality of projections, optimizing at least a portion of the plurality of projections yet to be delivered to the patient in substantially real-time to incorporate the analyzed information from the monitored machine parameters, the monitored changes to the patient, and the accumulated radiation dose; and
   delivering at least a portion of the plurality of projections yet to be delivered to the patient as optimized.

27. A method of delivering a radiation therapy treatment, the method comprising:
   generating a treatment plan for a patient, the treatment plan including a plurality of projections;
   positioning the patient to receive radiation from a radiation source based on the treatment plan;
   monitoring machine parameters during delivery of at least a portion of the plurality of projections in substantially real-time, the monitoring including analyzing information regarding the machine parameters and how the parameters affect dose delivered to the patient;
   during delivery of at least a portion of the plurality of projections, calculating an amount of accumulated radiation dose delivered to the patient in substantially real-time;
   during delivery of at least a portion of the plurality of projections, optimizing at least a portion of the plurality of projections yet to be delivered to the patient in substantially real-time to incorporate the analyzed information from the monitored machine parameters and the accumulated radiation dose, the optimizing including predicting machine parameters; and
   delivering at least a portion of the plurality of projections yet to be delivered to the patient as optimized.

28. The method of claim 1, wherein optimizing at least a portion of the plurality of projections yet to be delivered to the patient includes optimizing an open time of a plurality of leaves of a multi-collimator for at least a portion of the plurality of projections yet to be delivered to the patient in substantially real-time.

29. The method of claim 26, wherein optimizing at least a portion of the plurality of projections yet to be delivered to the patient includes optimizing an open time of a plurality of leaves of a multi-collimator for at least a portion of the plurality of projections yet to be delivered to the patient in substantially real-time.

30. The method of claim 27, wherein optimizing at least a portion of the plurality of projections yet to be delivered to the patient includes optimizing an open time of a plurality of leaves of a multi-collimator for at least a portion of the plurality of projections yet to be delivered to the patient in substantially real-time.

\* \* \* \* \*